_(12)_ United States Patent
Kamen et al.

(10) Patent No.: US 7,612,071 B2
(45) Date of Patent: Nov. 3, 2009

(54) COMPOSITIONS AND METHODS EMPLOYING AMINOPTERIN

(75) Inventors: Barton Aron Kamen, Princeton Junction, NJ (US); Peter David Cole, Montclair, NJ (US); Angela King Smith, West Windsor, NJ (US); John Anthony Zebala, Sammamish, WA (US)

(73) Assignee: Syntrix Biosystems, Inc., Auburn, WA (US)

( * ) Notice: Subject to any disclaimer, the term of this patent is extended or adjusted under 35 U.S.C. 154(b) by 0 days.

(21) Appl. No.: 11/078,614

(22) Filed: Mar. 9, 2005

(65) Prior Publication Data

US 2005/0209239 A1 Sep. 22, 2005

Related U.S. Application Data

(60) Provisional application No. 60/552,787, filed on Mar. 12, 2004.

(51) Int. Cl.
*A01N 43/54* (2006.01)
*A01N 43/60* (2006.01)
*A61K 31/4995* (2006.01)
*A61K 31/505* (2006.01)

(52) U.S. Cl. .................................................. 514/249
(58) Field of Classification Search ................. 514/249; 544/261
See application file for complete search history.

(56) References Cited

U.S. PATENT DOCUMENTS

| 2,443,165 A | | 6/1948 | Hultquist et al. |
| 2,575,168 A | | 11/1951 | Franklin |
| 4,077,957 A | | 3/1978 | Piper et al. |
| 4,079,056 A | | 3/1978 | Piper et al. |
| 5,766,481 A | * | 6/1998 | Zambias et al. ............. 210/656 |

OTHER PUBLICATIONS

Cecil, Textbook of Medicine, 21st Edition (2000), Goldman & Bennett (Editors), W.B. Saunders Company (Publisher), Chapter 198, pp. 1060-1074.*
Ratliff AF, et al., "Phase I and pharmacokinetic trial of aminopterin in patients with refractory malignancies," 1998 J Clin. Oncology, vol. 16(4): pp. 1458-1464.*
Mahoney DH, et al., "Acute neurotoxicity in children with B-precursor acute lymphoid leukemia," 1998 J Clin. Oncology, vol. 16(5): pp. 1712-1722.*
"Conversion Table of Body Weight (in Kg)," Apr. 10, 2002 <<http:www.vet.purdue.edu/vcs/Pcop/conversiontable.htm>>, printed from the internet on Sep. 5, 2005.*
Winick N, et al. "Intensive oral methotrexate protects against lymphoid marrow relapse in childhood B-precursor acute lymphoblastic leukemia," J Clin. Oncol. Oct. 1996, vol. 14(10): pp. 2803-2811.*
Aldrich Catalog (Aldrich®, 1996 Aldrich Chemical co., Inc., Milwaukee, WI, p. 93).*
Dacie et. al., "Aminopterin in the treatment of acute leukemia," British Medical Journal 1950, pp. 1447-1457; submitted by Applicant on the Aug. 8, 2005 IDS.*
Burchenal, J.H. et al. Studies on the chemotherapy of leukemia. 1949. Cancer. 2:113-118.

Dacie. J.V. et al. Aminopterin in the treatment of acute leukemia. B.M.J. 1:1447-1457.
Farber, S. et al. Advances in cancer research, pp. 2-73. New York Academic Press, New York, N.Y., 1956.
Glode, M. et al. A phase I study of high doses of aminopterin with leucovorin rescue in patients with advanced metastatic tumors. Can. Res. 1979. 39:3707-3714.
Goldin, A. et al. A quantitative comparison of the anti-leukemic effectiveness of two folic acid antagonists in mice. 1955. J. Natl. Cancer Inst. 5:1657-1664.
Heinrich, M.R. et al. Ion-exchange chromatography of pteroylglutamic acid and aminopterin. 1953. J. Am. Chem. Soc. 75:5425-5426.
Hutchinson, J.H. et al. Observations of the mechanisms of resistance to folic acid antagonists. 1953. Proc. Am. Assoc. Cancer Res. 1:26.
Loo, T.L. The purification of aminopterin. 1965. J. Med. Chem. 8:139.
Oliverio, V.T. Chromatographic separation and purification of folic acid analogs. Anal. Chem. 1961. 33(2):263-265.
Sacks, M.S. et al. The response of acute leukemia to the administration of the folic acid antagonists, aminopterin and amethopterin. 1950. Ann. Intern. Med. 32:80-115.
Seeger, D.R. et al. Analogs of pteroylglutamic acid. III. 4-amino derivatives. 1949. J. Am. Chem. Soc. 71:1753-1758.
Seeger. D.R. et al. Antagonist for pteroylglutamic acid. 1947. J. Am. Chem. Soc. 69:2567.
Sirotnak, F. & Donsbach. R. A basis for the difference in toxicity of methotrexate, aminopterin and methasquin in mice. Biochem. Pharmacol. 1975. 24: 156-158.
Waller, C.W. et al. Synthesis of pteroylglutamic acid (liver L. casei factor) and pteroic acid. 1948. J. Am. Chem. Soc. 70:19-22.
Weygand, F. et al. 1951. Z. Naturforsch. 6b:174.
Gubner, R. Therapeutic suppression of tissue reactivity. I. Comparison of the effects of cortisone and aminopterin. Am. J. Med. Sci. 221(2):169-175. Feb. 1951.
Gubner, R. Therapeutic supression of tissue reactivity. II. Effect of aminopterin in rheumatoid arthritis and psoriasis. Am. J. Med. Sci. 221(2):176-182. Feb. 1951.
Gubner, R. Effect of aminopterin on epithelial tissues. AMA Arch. Dermatol. Syphilol. 64(6):688-699. Dec. 1951.
Rees, RB, et al. Aminopterin for psoriasis. Arch. Dermatol. 90:544-552. Dec. 1964.

* cited by examiner

*Primary Examiner*—Ardin Marschel
*Assistant Examiner*—Amy A Lewis
(74) *Attorney, Agent, or Firm*—Jeffrey B. Oster

(57) ABSTRACT

The present invention relates to pharmaceutical compositions containing the antifolate aminopterin, processes for making the compositions, and methods of using them to treat disorders in adult and pediatric patients. Pharmaceutical compositions substantially free of impurities are provided comprising a therapeutically effective amount of aminopterin, or a pharmaceutically acceptable salt thereof. Relative to the teachings of the prior art, the disclosed methods and compositions provide unexpected improvements that include a greater interpatient oral bioavailability in pediatric patients, a smaller interpatient coefficient of variation of oral bioavailability, a smaller mean intrapatient coefficient of variation of oral bioavailability, a greater therapeutic index, a smaller coefficient of variation of toxicity, efficacy in combination therapy, and efficacy of certain polyglutamated metabolites.

3 Claims, No Drawings

COMPOSITIONS AND METHODS EMPLOYING AMINOPTERIN

The application claims the benefit of U.S. Provisional Patent application No. 60/552,787, filed Mar. 12, 2004.

This invention was developed with government funding from National Institutes of Health. The federal government may have certain rights in the invention.

FIELD OF THE INVENTION

The present invention relates to pharmaceutical compositions containing the antifolate aminopterin, processes for making the compositions, and methods of using them to treat disorders in adult and pediatric patients. We have discovered aminopterin compositions and methods not provided for in the prior art, or that perform differently and unexpectedly from the teachings of the prior art. In particular, pharmaceutical compositions substantially free of impurities are provided comprising a therapeutically effective amount of aminopterin, or a pharmaceutically acceptable salt thereof.

BACKGROUND OF THE INVENTION

Aminopterin, or N-4-[[2,4-diamino-6-pteridinyl)-methyl]amino]benzoyl]-L-glutamic acid, is a potent antifolate [see Franklin, U.S. No. Pat. No. 2,575,168]. Synthesized in 1946 by the American Cyanamid Co. (later the Lederle Laboratories), aminopterin was one of the first antifolates developed and the first to demonstrate significant clinical efficacy [see Seeger et al., *J. Am. Chem. Soc.* 69:2567, 1947 and Farber et al., *N. Engl. J. Med.* 238:787, 1948]. Other structurally related antifolates, including methotrexate, were described by the Lederle Laboratories in the ensuing years between 1948 and 1955. Compared to all other antifolates, aminopterin bears the closest structural similarity to folic acid, differing from the natural substrate by only two atoms.

Aminopterin was used clinically as a single agent in the 1940s and 1950s for the treatment of acute leukemia, psoriasis and arthritis in humans [see Farber et al., *N. Engl. J. Med.* 238:787, 1948; Gubner, *Arch. Derm., Chicago* 64:688, 1951; Rees et al., *Arch. Derm., Chicago* 90:544, 1964; and Gubner et al., *Am. J. Med Sci.* 22:176, 1951]. The prior art provides no teachings on the use of aminopterin to treat cancer, leukemia, arthritis psoriasis and other inflammatory disorder using modern combination therapy. Based mainly on the results from animal studies and anecdotal human experience, its clinical use ceased in the mid-1950s when aminopterin was determined to have inferior pharmacologic properties to methotrexate.

In particular, the prior art teaches that methotrexate has a less variable toxicity and a greater therapeutic index than aminopterin [see Burchenal et al., *Cancer* 2:113, 1949; Farber et al., *Advances in Cancer research*, pp 2-73. New York: Academic Press, 1956; Dacie et al., *B. M. J.* 1:1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979]. In other teaching methotrexate is suggested to be less toxic and efficacious than aminopterin in treating psoriasis, however the doses compared were not equipotent to one another, with methotrexate being used in an amount 4-fold less than would be required to be equipotent with aminopterin [Rees and Bennett, *Arch. Dermatol.* 83:970-72, June 1961; and Strakosch, Dermatologica 126: 259-267, 1963]. Thus, by modern standards no conclusions could be drawn regarding their relative efficacy, toxicity, or therapeutic index. Later, Rees et al. suggest the opposite, that methotrexate may be more safe and efficacious than aminopterin in treating psoriasis [Rees et al., *Arch. Dermatol.* 90:544-52, December 1964]. Accordingly, the art abandoned aminopterin for methotrexate around 1955, and methotrexate has since become the standard antifolate used in the treatment of neoplastic and inflammatory disorders that include, but are not limited to leukemia, breast cancer, squamous cell tumors of the head and neck, choriocarcinoma, psoriasis, asthma, and arthritis [see Piper and Montgomery, U.S. Pat. Nos. 4,077, 957 and 4,079,056].

Despite the widespread clinical use of methotrexate, there remains several shortcomings with its use as a human therapeutic. First, at oral doses greater than about 7.5 mg/m$^2$, the bioavailability of methotrexate is 44% or less [see Balis, et al., *Cancer Res.* 43(5):2342, 1983; Balis, et al., *Blood*, 92(10): 3569, 1998; Kearney, et al., *Cancer Chemother. Pharmacol.* 3(2):117, 1979; Pinkerton, et al., *Br. J. Cancer* 45(2):300, 1982; and Pinkerton, et al., *Cancer Chemother. Pharmacol.* 10(1):36, 1982]. Above a dose of about 15 mg/m$^2$, absorption from the gastrointestinal tract is saturable, such that if the dose of methotrexate is increased, the fraction absorbed declines [see Balis, et al., *J. Clin. Oncol.*, 6(12):1882, 1988 and Campbell, et al., *Cancer Treat. Rep.*, 69(7-8):833, 1985]. Second, the bioavailability of an oral methotrexate dose greater than about 7.5 mg/m$^2$ is highly variable both in the same patient and between different patients, with peak plasma concentrations occurring from 0.5 to 5 hours after oral administration, and the percentage of a dose absorbed ranging from 5% to 97% [see Balis, et al., *Cancer Res.* 43(5):2342, 1983]. Third, a significant fraction of the population does not respond to methotrexate treatment in combination therapy [see Wallace, *Clin. Exp. Rheumatol.*, 17:499, 1999; Ravelli and Martini, *J. Rheumatol.* 27(8):1830, 2000; and Campbell, et al., *Cancer Treat. Rep.*, 69(7-8):833, 1985]. Finally, patient compliance, particularly in pediatric patients, can be problematic due to the large number of tablets required in a particular methotrexate dosage.

It is known in the art that aminopterin has greater oral bioavailability than methotrexate in adults (~85%), has efficacy as a single agent in some patients with T-lineage leukemia refractory to conventional therapy employing methotrexate, and is at least about 10 times more potent than methotrexate [see Ratliff et al., *J. Clin. One.* 16:1458, 1998; Glode et al., *Cancer Res.* 39:3707, 1979; Cole et al., *Proc. Am. Assoc. Cancer Res.* 43:749, 2002; and Sirotnak and Donsback, *Cancer Res.* 32:2120, 1972]. However, the prior art provides no teachings on the oral bioavailability of aminopterin in pediatric patients, variability of oral bioavailability in the same patient, variability of oral bioavailability in different patients, or the efficacy of aminopterin in treating a variety of cancers or inflammatory diseases using modern combination therapy.

The prior art also teaches that any utility aminopterin might have is mitigated by a more narrow therapeutic index and more variable toxicity relative to methotrexate [see Burchenal et al., *Cancer* 2:113, 1949; Farber et al., *Advances in Cancer research*, pp 2-73. New York: Academic Press, 1956; Dacie et al., *B. M. J* 1:1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979]. Accordingly, there is also a need in the art for an antifolate alternative to methotrexate which compared to methotrexate, has an equivalent or greater therapeutic index, and an equivalent or smaller coefficient of variation of toxicity.

It is known that methotrexate is metabolized to various polyglutamated species and that the number of glutamates in the polyglutamate chain of a particular species is proportional to its efficacy in cell-based and enzyme systems [see Allegra, et al., *Proc. Natl. Acad. Sci. U.S.A.*, 82:4881, 1985; Sirotnak and Donsback, *Cancer Res.* 32:2120, 1972; and Ratliff et al., *J. Clin. Oncol.* 16:1458, 1998]. Thus the art suggests that longer polyglutamate chains should improve clinical efficacy of an antifolate. However, there are no teachings that this is relevant clinically, or whether another combination of species, including those with polyglutamate chains with fewer glutamates, might provide for an antifolate with greater efficacy.

Rees et al. noted in 1964 that aminopterin is even less pure than methotrexate and that instability was a problem [Rees et al., *Arch. Dermatol.* 90:544-52, December 1964]. It is also known that the aminopterin within pharmaceutical compositions of the prior art were made via a one-pot aqueous condensation of a pteridine with p-aminobenzoic acid and glutamate, and contained variable amounts of impurities, mostly contaminating folic acid, that represented up to 41 weight percent of a preparation [see Franklin, U.S. Pat. No. 2,575,168; Seeger, et al., *J. Am. Chem. Soc.* 69:2567, 1947; Seeger, et al., *J. Am. Chem. Soc.* 71:1753, 1949; Sirotnak and Donsbach, *Biochem. Pharmacol.* 24:156, 1975; Loo, *J. Med. Chem.* 8:139, 1965; Heinrich et al., *J. Am. Chem. Soc.* 75:5425; Weygand et al., *Naturforsch.* 6b: 174, 1951; Hutchinson and Burchenal, *Proc. Am. Assoc. Cancer Res.* 1:26, 1953; Waller, et al., *J. Am. Chem. Soc.* 70:19, 1948; and Hultquist and Dreisbach, U.S. Pat. No. 2,443,165]. The prior art teaches that the simultaneous co-administration of folic acid and aminopterin had no effect on toxicity, the predictability of toxicity, or the therapeutic index of aminopterin [see Nichol and Welch, *Proc. Soc. Exp. Biol. Med.* 74:403, 1950; Golden et al., *Cancer Res.* 13:843, 1953; Greenspan et al., *Cancer* 3:856, 1950; Franklin et al., *Proc. Soc. Exp. Biol. Med.* 5:1, 1948; Schoenback et al., *J.A.M.A.* 144:1558, 1950; Dameshek, *Blood* 4:168, 1949; Farber, *Blood* 4:160, 1949; and Dameshek et al., *Blood* 5:898, 1950].

There are no teachings in the prior art on how to prepare pharmaceutical compositions having greater aminopterin purity or consistent aminopterin purity, or how to use such compositions therapeutically to obtain greater interpatient oral bioavailability in pediatric patients, a smaller interpatient coefficient of variation of oral bioavailability, a smaller mean intrapatient coefficient of variation of oral bioavailability, a greater therapeutic index, a smaller coefficient of variation of toxicity, efficacy in combination therapy, and efficacy of certain polyglutamated metabolites.

SUMMARY OF THE INVENTION

Accordingly, there is a need in the art for pharmaceutical compositions of aminopterin that are substantially free of impurities and/or that have consistent aminopterin purity. There is also a need in the art for an antifolate alternative to methotrexate which has greater oral bioavailability, has less variable oral bioavailability both in the same patient (intrapatient) and between different patients (interpatient), is efficacious in combination therapy, and/or has greater potency and therefore requires fewer tablets for a particular dosage so as to improve patient compliance. Further, there is a need for methods of using aminopterin therapeutically that are not provided for in the teachings of the prior art, and that provide advantages over previously described methods of using aminopterin or methotrexate. The present invention fulfills these needs and further provides other related advantages.

Briefly stated, an embodiment of the present invention provides compositions and methods for treating a patient with a therapeutically effective amount of aminopterin, or a pharmaceutically acceptable salt thereof. Within certain embodiments, the present invention provides a method for treating a disorder in a pediatric patient with an antifolate having greater interpatient oral bioavailability than methotrexate, which comprises orally administering to said pediatric patient a therapeutically effective amount of aminopterin, or a pharmaceutically acceptable salt thereof. An embodiment of the present invention also provides a pharmaceutical composition comprising a therapeutically effective amount of aminopterin, or a pharmaceutically acceptable salt thereof, wherein the interpatient oral bioavailability of the aminopterin in a pediatric patient is greater than the interpatient oral bioavailability of methotrexate in a pediatric patient. In certain embodiments the interpatient oral bioavailability is greater than 60%, 70%, 80%, and more preferably greater than 90%. In other embodiments the aminopterin may be administered with at least one therapeutically effective dose of leucovorin. In still other embodiments, the pharmaceutical composition is substantially free of impurities.

An embodiment of the present invention further provides methods of treating a disorder in a human with an antifolate having a smaller interpatient coefficient of variation of oral bioavailability than the interpatient coefficient of variation of oral bioavailability of methotrexate, which comprises orally administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the interpatient coefficient of variation of oral bioavailability is smaller than the interpatient coefficient of variation of oral bioavailability of methotrexate. In some embodiments, the interpatient coefficient of variation of oral bioavailability is less than 55%, and more preferably less than 45%. In other embodiments, the therapeutically effective amount of aminopterin is from 0.2 milligrams to 2.0 milligrams.

An embodiment of the present invention further provides methods of treating a disorder in a human with an antifolate having a smaller mean intrapatient coefficient of variation of oral bioavailability than the mean intrapatient coefficient of variation of oral bioavailability of methotrexate, which comprises orally administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the mean intrapatient coefficient of variation of oral bioavailability is smaller than the mean intrapatient coefficient of variation of oral bioavailability of methotrexate. In some embodiments, the mean intrapatient coefficient of variation of oral bioavailability is less than 30%, and more preferably less than 25%. In other embodiments, the therapeutically effective amount of aminopterin required for a level of efficacy is less than the therapeutically effective amount of methotrexate required for the same level of efficacy.

Within further aspects, the present invention provides methods for treating a disorder in a human with an antifolate having an equivalent or greater therapeutic index than the corresponding therapeutic index of methotrexate, which comprises administering to said human a therapeutically effective amount of aminopterin, or a pharmaceutically acceptable salt thereof. An embodiment of the invention also provides for a pharmaceutical composition comprising a therapeutically effective amount of aminopterin, or a pharmaceutically acceptable salt thereof, wherein the therapeutic index is equal to or greater than the corresponding therapeutic index of methotrexate.

An embodiment of the present invention further provides methods of treating a disorder in a human with an antifolate having an equivalent or smaller coefficient of variation of toxicity than the corresponding coefficient of variation of toxicity of methotrexate, which comprises administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the coefficient of variation of toxicity is equal to or smaller than the corresponding coefficient of variation of toxicity of methotrexate. In some embodiments, the pharmaceutical composition is substantially free of impurities and contains a therapeutically effective amount of aminopterin that has a standard deviation of less than 5%.

An embodiment of the present invention further provides methods of treating a disorder in a patient using combination therapy, which comprises administering to said patient a therapeutically effective amount of aminopterin, or a pharmaceutically acceptable salt thereof, according to a therapeutic protocol involving at least one other therapeutic. The at least one other therapeutic may be administered prior to, contemporaneous with, or after administering the aminopterin. The at least one other therapeutic can be, for example, prednisone, a cox-2 inhibitor, a non-steroidal anti-inflammatory drug, vincristine, asparaginase, daunorubicin, mercaptopurine, etoposide and cytarabine. The disorder in some embodiments can include acute leukemia, acute lymphoblastic leukemia, B lineage acute lymphoblastic leukemia, T lineage acute lymphoblastic leukemia, acute myeloblastic leukemia, relapsed leukemia, refractory leukemia, breast cancer, squamous cell tumors of the head and neck, choriocarcinoma, endometrial cancer, arthritis, rheumatoid arthritis, juvenile rheumatoid arthritis, and psoriasis.

An embodiment of the present invention further provides methods of treating a disorder in a human with an antifolate that is metabolized to a polyglutamate having a different relative frequency than the relative frequency of the corresponding methotrexate polyglutamate, which comprises administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the aminopterin is metabolized to a polyglutamate having a different relative frequency than the relative frequency of the corresponding methotrexate polyglutamate. In some embodiments, the aminopterin is metabolized to two, three and more preferably four polyglutamates each having a different relative frequency than the relative frequency of the corresponding methotrexate polyglutamates. In other embodiments, the aminopterin polyglutamates have a smaller weighted average chain length than the weighted average chain length of the corresponding methotrexate polyglutamates. In still other embodiments, the aminopterin polyglutamate having a total of two attached glutamates is the majority polyglutamate.

An embodiment of the present invention further provides methods of treating a disorder in a human, which comprises administering to said human an active pharmaceutical ingredient substantially free of impurities, wherein the antifolate in the active pharmaceutical ingredient is a therapeutically effective amount of aminopterin, or a pharmaceutically acceptable salt thereof. Also provided are pharmaceutical compositions substantially free of impurities and comprising an active pharmaceutical ingredient, wherein the antifolate in the active pharmaceutical ingredient is a therapeutically effective amount of aminopterin, or a pharmaceutically acceptable salt thereof. In some embodiments, the pharmaceutical composition is substantially free of impurities that include, for example, folic acid, pterins, and conjugates of p-aminobenzoic acid. In preferred embodiments, the aminopterin purity in the active pharmaceutical ingredient is equal to or greater than 95 area %, greater than 95 weight %, or greater than 95 mole %. In other embodiments, the pharmaceutical composition has less than 5 area %, less than 5 weight %, or less than 5 mole % impurities. In still other embodiments, pharmaceutical compositions contain a therapeutically effective amount of aminopterin with a standard deviation of less than 5%.

These and other aspects of the present invention will become apparent upon reference to the detailed description and illustrative examples which are intended to exemplify non-limiting embodiments of the invention. All references disclosed herein are hereby incorporated by reference in their entirety as if each was incorporated individually.

GLOSSARY

Prior to setting forth the invention in detail, it may be helpful to an understanding thereof to set forth definitions of certain terms that will be used hereinafter.

The term "active pharmaceutical ingredient" as used herein means a mixture of an antifolate and impurities resulting from one or more organic synthetic steps. An organic synthetic step will comprise the partial or complete transformation of one or more chemicals to one or more new chemicals, and will also usually entail at least one or more purification steps to enrich the one or more new chemicals. The one or more purification steps will consist of methods known to those skilled in the art, such as, for example, crystallization, extraction, and chromatography. Ideally, purification steps are not required, or the one or more purification steps will enrich a single new chemical preferentially. For example, an active pharmaceutical ingredient containing aminopterin is made by the transformation of 2,4-diamino-6-(bromomethyl)pteridine and N-(4-aminobenzoyl)-L-glutamic acid in dimethylacetamide to aminopterin plus several impurities, wherein the impurities comprise at least folic acid and untransformed 2,4-diamino-6-(bromomethyl)pteridine and N-(4-aminobenzoyl)-L-glutamic acid.

The term "aminopterin purity" as used herein means the percentage of antifolate in an active pharmaceutical ingredient or pharmaceutical composition, wherein the antifolate is aminopterin (see glossary definition of "impurities").

The term "antifolate" as used herein means a molecule and/or metabolites of the molecule that interfere with the normal metabolism or utilization of folic acid (i.e. folate) and/or metabolites of folic acid in a cell-free biochemical system or in cells found in cell culture, tissue culture, leukemia, cancer, a mammal, and a human. For example, aminopterin and methotrexate, as well as their polyglutamated metabolites, are antifolates. Typically, an antifolate and/or metabolite of the antifolate will interfere with the normal metabolism or utilization of folic acid and/or metabolites of folic acid by blocking their binding to one or more enzymes or receptors that include, for example, the reduced folate receptor, the folic acid receptor, folylpolyglutamate synthase, dihydrofolate reductase, thymidylate synthase, methylene-tetrahydrofolate reductase, amido phosphoribosyltransferase, glycinamide ribonucleotide transformylase, aminoimidazole carboxamide ribonucleotide transformylase, and homocysteine methyltransferase. Examples of folic acid metabolites that an antifolate and/or metabolites of the antifolate will interfere with include, but are not limited to, 5-methyltetrahydrofolate-(glu)$_n$, 5,10-methylene-tetrahydrofolate-(glu)$_n$, tetrahydrofolate-(glu)$_n$, N-5-fomamino-tetrahydrofolate-(glu)$_n$, 5,10-methenyl-tetrahydrofolate-(glu)$_n$, 10-formyl-tetrahydrofolate-(glu)$_n$, and 5-formyl-tetrahydrofolate-(glu)$_n$, where -(glu)$_n$ refers to the glutamates attached to the metabolite and n is the number of attached glutamates. When n=1, no glutamates have been added to these folic acid metabolites beyond that found in the original folic acid molecule. When n is greater than 1 these folic acid metabolites are considered to be polyglutamates (see glossary term below).

The term "AUC" as used herein means the area under the plasma concentration-time curve for a single dose of a drug as described more fully in Shargel and Yu, *Applied Biopharmaceutics and Pharmacokinetics*, 4$^{th}$ Edition, 1999, Appleton & Lange, Stamford, Conn., incorporated herein by reference. The AUC is proportional to the amount of drug that reaches the plasma.

The term "coefficient of variation" as used herein refers to the standard deviation of a population divided by the population mean and expressed as a percentage. It describes the relative variability of a population.

The term "coefficient of variation of toxicity" as used herein refers to the coefficient of variation of the magnitude of a particular toxicity manifestation. It will be understood by a skilled practitioner that the determination of the coefficient of variation of toxicity of an antifolate, such as aminopterin, need not be determined for every patient in a population treated according to the invention. It is sufficient to use a representative number of patients from a particular patient population to establish a coefficient of variation of toxicity for that population, where at least 5 patients will be required in order to establish a coefficient of variation of toxicity of a population.

The term "combination therapy" as used herein refers to the use of two or more therapeutics according to a therapeutic protocol with the aim of providing a highly optimized treatment plan to most effectively treat a disorder in a patient.

The term "disease manifestation" as used herein refers to any undesired result of a disorder. Particular disease manifestations include, but are not limited to peripheral blasts, bone marrow infiltrates by malignant cells, blasts in the central nervous system, lethargy, joint pain, joint inflammation, joint damage, inflammatory cells in joint fluid, cancer and psoriatic skin lesions.

The term "efficacy" as used herein means an antifolate is therapeutically effective. Generally, a greater level of efficacy will be achieved by increasing the dose and/or frequency of administration of an antifolate given to a population, such that a greater proportion of the population will receive a benefit and/or there will be a greater magnitude of benefit in an individual patient. If a first antifolate is more potent than a second antifolate, it will reach a greater level of efficacy than the second antifolate using identical amounts of each.

The term "disorder" as used herein refers to a disease afflicting an adult or pediatric human or animal. The disorder will typically be neoplastic or inflammatory, and may comprise, for example, acute leukemia, acute lymphoblastic leukemia, B lineage acute lymphoblastic leukemia, T lineage acute lymphoblastic leukemia, acute myeloblastic leukemia, relapsed leukemia, refractory leukemia, breast cancer, squamous cell tumors of the head and neck, choriocarcinoma, endometrial cancer, arthritis of undefined etiology, rheumatoid arthritis, juvenile rheumatoid arthritis, and psoriasis.

The term "impurities" as used herein refers to the impurities found in the active pharmaceutical ingredient. Impurities arise during the organic synthetic steps employed in the preparation of the active pharmaceutical ingredient, and in the case of aminopterin include, for example, folic acid, pterins, and conjugates of p-aminobenzoic acid (i.e. pABAglu). Impurities may be the result of incomplete transformation of chemicals during an organic synthetic step, or one or more side-reactions that result in chemicals being transformed into unintended new chemicals. As defined herein, the pharmaceutically acceptable carriers and optional therapeutic ingredients in a pharmaceutical composition do not constitute impurities. Impurities in a pharmaceutical composition pertain only to those impurities in the active pharmaceutical ingredient used to make the pharmaceutical composition. Impurities are quantitated using any measurable property suitable for quantitating molecules. Such measurable properties will be familiar to those in the art and include, for example, HPLC peak area (i.e. "area"), mass and moles. Impurities will typically be conveniently quantitated based on their area, but may also be quantitated according to their weight or moles using, for example, uv absorbance of collected HPLC peak fractions and the known extinction coefficient and molecular weight of each impurity. If the molecular weight of an impurity is unknown, mass spectrometry may be used. The percentage of an impurity in an active pharmaceutical ingredient or pharmaceutical composition is the amount of the impurity divided by the total amount of impurities plus antifolate multiplied by 100, wherein all impurities and the antifolate are quantitated using the same measurable property. For example, the percentage of an impurity in an active pharmaceutical ingredient or pharmaceutical composition may be expressed as an area %, weight %, or mole %. In a specific example, if an impurity constitutes 0.1 micromole of an active pharmaceutical ingredient and the aminopterin plus total impurities in the active pharmaceutical ingredient together constitute 1 micromole, the percentage of the impurity in the active pharmaceutical ingredient is 10 mole %. In another example, if an impurity is 0.25 area units of a pharmaceutical composition and the total impurities plus antifolate together are 1.0 area units of the pharmaceutical composition, the percentage of the impurity in the pharmaceutical composition (or the active pharmaceutical ingredient) is 25 area %. In a further example, if an impurity is 0.04 mg of a pharmaceutical composition containing 2 mg of the active pharmaceutical ingredient, the percentage of the impurity in the pharmaceutical composition is 2 weight %. The percentage of total impurities may be obtained by summing the percentages of all individual impurities in the active pharmaceutical ingredient or pharmaceutical composition, wherein all the individual impurities are quantitated using the same measurable property. The percentage of antifolate in an active pharmaceutical ingredient or pharmaceutical composition is the amount of antifolate divided by the total amount of impurities plus antifolate multiplied by 100, wherein all impurities and the antifolate are quantitated using the same measurable property. Thus, the percentage of total impurities in the active pharmaceutical ingredient or pharmaceutical composition may alternatively be obtained by subtracting the percentage of antifolate from 100%.

The term "interpatient coefficient of variation of oral bioavailability" as used herein refers to the coefficient of variation of oral bioavailability in a population of at least two patients, wherein the oral bioavailability is determined at least once for each patient in the population. Specifically, it is the standard deviation of oral bioavailability in the population divided by the interpatient oral bioavailability, expressed as a percent. It will be understood by a skilled practitioner that the determination of the interpatient coefficient of variation of oral bioavailability of an antifolate, such as aminopterin, need not be determined for every patient in a population treated according to the invention. It is sufficient to use a representative number of patients from a particular patient population to establish the interpatient coefficient of variation of oral bioavailability for that population, where at least 5 patients will be required in order to establish the interpatient coefficient of variation of oral bioavailability of a population.

The term "interpatient oral bioavailability" as used herein refers to the mean oral bioavailability in a population of at least two patients, wherein the oral bioavailability is determined at least once for each patient in the population. The interpatient oral bioavailability may be calculated by dividing the mean population AUC after oral dosing by the mean population AUC after intravenous dosing, wherein the oral and intravenous doses are identical, and expressing the ratio as a percent. In a preferred method, the interpatient oral bioavailability is calculated using matched samples by averaging the oral bioavailabilities obtained for each patient. More specifically, the oral bioavailability is obtained for each patient by dividing the AUC after oral dosing the patient by the AUC after intravenous dosing the same patient with the same dose of antifolate (i.e. the oral and intravenous AUC in each patient are matched and the patients are said to be matched). The interpatient oral bioavailability based on these matched patients is then simply the mean population oral bioavailability expressed as a percent. It will be understood by a skilled practitioner that the determination of the interpatient oral bioavailability of an antifolate, such as aminopterin, need not be determined for every patient in a population treated according to the invention. It is sufficient to use a representative number of patients from a particular patient population to establish an interpatient oral bioavailability for that population, where at least 5 patients will be required in order to establish an interpatient oral bioavailability of a population.

The term "intrapatient coefficient of variation of oral bioavailability" as used herein refers to the coefficient of variation of oral bioavailability of two or more antifolate doses given to the same patient. Specifically, it is the standard deviation of oral bioavailability of the two or more antifolate doses in the same patient divided by the intrapatient oral bioavailability, expressed as a percent.

The term "intrapatient oral bioavailability" as used herein refers to the average oral bioavailability of multiple antifolate doses given to the same patient. For example, the oral bioavailability is determined for each of two or more doses of an antifolate, wherein the period between doses is at least ten half lives so as to insure complete elimination of a prior dose. The average oral bioavailability of the two or more doses is then calculated and expressed as a percent to provide the intrapatient oral bioavailability.

The term "mean intrapatient coefficient of variation of oral bioavailability" as used herein refers to the average intrapatient coefficient of variation of oral bioavailability for two or more patients. It will be understood by a skilled practitioner that the determination of the mean intrapatient coefficient of variation of oral bioavailability of an antifolate, such as aminopterin, need not be determined for every patient in a population treated according to the invention. It is sufficient to use a representative number of patients from a particular patient population to establish a mean intrapatient coefficient of variation of oral bioavailability for that population, where at least 5 patients will be required in order to establish a mean intrapatient coefficient of variation of oral bioavailability of a population.

The term "oral bioavailability" as used herein refers to the fraction of an antifolate dose given orally that is absorbed into the plasma after a single administration to a patient. A preferred method for determining the oral bioavailability is by dividing the AUC of an antifolate dose given orally by the AUC of the same antifolate dose given intravenously to the same patient, and expressing the ratio as a percent. Other methods for calculating oral bioavailability will be familiar to those skilled in the art, and are described in greater detail in Shargel and Yu, *Applied Biopharmaceutics and Pharmacokinetics*, $4^{th}$ Edition, 1999, Appleton & Lange, Stamford, Conn., incorporated herein by reference.

The term "pharmaceutical composition" as used herein means the active pharmaceutical ingredient combined with one or more pharmaceutically acceptable carriers, and optionally other therapeutic ingredients. Suitable pharmaceutically acceptable carriers will be familiar to those skilled in the art, and will comprise, for example, microcrystalline cellulose, lactose, silicon dioxide, croscarmellose, sodium benzoate, sorbitol, magnesium stearate and flavoring. The active pharmaceutical ingredient will typically comprise only a small percentage of the total pharmaceutical composition. For example, a "2 mg aminopterin tablet" is a pharmaceutical composition that weighs about 100 mg, and comprises about 98 grams of pharmaceutically acceptable carriers and about 2 mg of the active pharmaceutical ingredient. The 2 mg of the active pharmaceutical ingredient consists mostly of aminopterin and a small fraction of impurities (see glossary definition of "impurities" and "active pharmaceutical ingredient"). If this pharmaceutical composition is said to be "substantially free of impurities", then the small fraction of impurities will be, for example, less than 5 area %, less than 5 weight %, or less than 5 mole % percent of the active pharmaceutical ingredient (see glossary definition of "substantially free of impurities").

The term "polyglutamates" as used herein refers to folate and antifolate metabolites that have attached two or more glutamates. The enzyme folylpolyglutamate synthase attaches additional glutamates to folate metabolites and some antifolates beyond the glutamate that is on the original folate metabolite and some antifolates to form a polyglutamate chain. Examples of aminopterin and methotrexate polyglutamates include aminopterin-$(glu)_n$ and methotrexate-$(glu)_n$, where $-(glu)_n$ refers to the glutamates attached to the antifolate and n is the number of attached glutamates. When n=1, no glutamates have been added beyond that in the original antifolate molecule. When n is greater than 1 these antifolate are considered to be polyglutamates, and thus have a polyglutamate chain. A polyglutamate chain is said to have a length, wherein a first polyglutamate chain is said to have a longer length than a second polyglutamate chain if the n of the first polyglutamate chain is larger than the n of the second polyglutamate chain. Folate and antifolate metabolites having polyglutamate chains are often referred to as polyglutamated species or polyglutamates. A mixture of polyglutamate chains having different lengths is said to comprise polyglutamate chain lengths. Both aminopterin and methotrexate are metabolized to polyglutamates having an n of from 2 to about 5, as described in greater detail in, Gangjee et al., *Curr. Med. Chem. Anti-Canc. Agents.* 2(3):331, 2002, incorporated herein by reference.

The term "potency" as used herein means the effectiveness of a dosage to achieve a particular level of efficacy. The dosage takes into account the amount of drug given at each administration (i.e. dose), the frequency of administration, and optionally, the total number of doses to be given. The effectiveness of a dosage can be quantitated by measuring the cumulative amount of drug administered in a defined period (i.e. the "dose rate") of the dosage and that results in a particular level of efficacy, where effectiveness and potency are inversely related to the dose rate. A first drug whose dosage has greater effectiveness or potency than the dosage of a second drug is said to be more potent than the second drug. For example, a first antifolate is more potent than a second antifolate if both achieve the same level of efficacy using a dose rate that is smaller in the first antifolate than the second antifolate. In a more specific example, a first antifolate is more potent than a second antifolate if both achieve the same level of efficacy using a dosage that is identical except for the dose of the first antifolate being smaller than the dose of the second antifolate. In a further example, a first antifolate is more potent than a second antifolate if both achieve the same level of efficacy using a dosage that is identical except for the frequency of administration of the first antifolate being smaller than the frequency of administration of the second antifolate. Two different antifolates may have different potencies, and will therefore achieve the same level of efficacy at different therapeutically effective amounts. For example, aminopterin is about 25 times more potent than methotrexate, and therefore the therapeutically effective amount of aminopterin required for a level of efficacy is about 25-fold less than the therapeutically effective amount of methotrexate required for the same level of efficacy. The therapeutically effective amounts of two antifolates (i.e. either as a dosage or as a single dose) that result generally in the same level of efficacy are referred to herein as equi-potent. For example, two oral doses of 2 mg/m$^2$ aminopterin are approximately equi-potent to four oral doses of 25 mg/m$^2$ methotrexate.

The term "relative frequency" as used herein means the fraction of a mixture of an antifolate and its polyglutamates that has a particular n number of glutamates attached. The fraction may be of any measurable quantity of the antifolate and its polyglutamates such as mass, moles, or HPLC peak area. The fraction may also be represented as a percent. For example, a mixture of aminopterin-(glu)$_n$ species obtained from a patient's leukemic cells may consist of 5% (n=1), 70% (n=2), 15% (n=3), 5% (n=4) and 5% (n=5). In this example, the n=1 parent drug is said to have a relative frequency of 5%, the n=2 polyglutamate is said to have a relative frequency of 70%, and the n=4 polyglutamate is said to have a relative frequency of 5%. The relative frequencies of polyglutamates may be determined using, for example, a cell culture or xenograft animal model of a particular disorder, or patient cells directly or indirectly involved in causing the disorder. The relative frequency may be from a single determination (e.g. a patient) or an average from a population (e.g. a population of patients or samples from a disorder). Methods for measuring the relative frequency of an antifolate and its polyglutamates will be familiar to those in the art and will typically employ the addition of tritiated antifolate (e.g. aminopterin or methotrexate) followed by high-pressure liquid chromatography (HPLC). Such methods are described in greater detail in Kamen and Winick, *Methods Enzymol.*, 122: 339, 1986 and Smith et al., *Clin. Cancer Res.*, 2:69, 1996, incorporated herein by reference. It will be understood by a skilled practitioner that the determination of a relative frequency of an antifolate, such as aminopterin, need not be determined for every patient in a population treated for a disorder according to the invention. It is sufficient to use samples from a representative number of patients with a particular disorder to establish a relative frequency for that disorder, where samples from at least 5 patients with the disorder will be required in order to establish a relative frequency in the disorder.

The term "substantially free of impurities" as used herein means that the percentage of total impurities in an active pharmaceutical ingredient or in a pharmaceutical composition is less than five percent (see definition of "impurities"). For example, a pharmaceutical composition or active pharmaceutical ingredient is said to be substantially free of impurities if the percentage of total impurities is less than 5 area %, 5 weight % or 5 mole %. As used herein, "substantially free of impurities" also means that the percentage of antifolate in an active pharmaceutical ingredient or in a pharmaceutical composition is ninety-five percent or greater (see definition of "impurities"). For example, a pharmaceutical composition that has a percentage of antifolate with an area %, weight %, or mole % equal to or greater than ninety-five, is said to be substantially free of impurities. In a more specific example, a pharmaceutical composition or active pharmaceutical ingredient that has an aminopterin purity with an area %, weight %, or mole % equal to or greater than ninety-five, is said to be substantially free of impurities.

The term "therapeutic benefit" as used herein refers to any parameter during therapy that is beneficial to a patient, wherein the parameter can include, but is not limited to inter-patient variability in oral bioavailability, intrapatient variability in oral bioavailability, therapeutic index, variability in toxicity, efficacy in combination therapy, and efficacy of certain polyglutamates.

The term "therapeutic component" as used herein refers to a therapeutically effective dosage (i.e. dose and frequency of administration) that eliminates, reduces, or prevents the progression of a particular disease manifestation in a percentage of a population. An example of a commonly used therapeutic component is the $ED_{50}$, which describes the dose in a particular dosage that is therapeutically effective for a particular disease manifestation in 50% of a population.

The term "therapeutic index" as used herein refers to the ratio of a particular toxicity component (i.e. the dose that is toxic in a percentage of a population, for example, the $TD_{50}$) to a particular therapeutic component (i.e. the dose that is effective in percentage of a population, for example, the $ED_{50}$). It will be understood by a skilled practitioner that the determination of the therapeutic index of an antifolate, such as aminopterin, need not be determined for every patient in a population with a disorder treated according to the invention. It is sufficient to use a representative number of patients with the disorder to establish a therapeutic index for the entire patient population with the disorder, where at least 5 patients with the disorder will be required in order to establish a therapeutic index for the entire patient population with the disorder.

The term "therapeutic protocol" as used herein refers to a schedule of dosing, routes of administration, and schedule duration for two or more drugs that are employed within combination therapy. The schedule may be further divided into specific phases each of a specified duration. For example, the induction, consolidation, intensive continuation and continuation phases of modern pediatric ALL treatment constitute specific phases of a therapeutic protocol. During each phase, the type of drugs to be given, their dosing, and routes of dosing are defined for all patients in general or may be modified based on other disease factors such a laboratory or imaging tests.

The term "therapeutically effective amount" as used herein means the dosage (dose or amount, and frequency) of antifolate which directly or indirectly kills neoplastic cells, arrests new cell growth, or reduces new cell growth in a human or other mammal afflicted with a neoplastic disorder such as, for example, acute leukemia, acute lymphoblastic leukemia, B lineage acute lymphoblastic leukemia, T lineage acute lymphoblastic leukemia, acute myeloblastic leukemia, relapsed leukemia, refractory leukemia, breast cancer, squamous cell tumors of the head and neck, choriocarcinoma, and endometrial cancer. The term as used herein shall also mean the dosage of antifolate which directly or indirectly kills inflammatory cells, arrests the accumulation of inflammatory cells, or reduces the accumulation of inflammatory cells in a human or other mammal afflicted with an inflammatory disorder such as, for example, arthritis of undefined etiology, rheumatoid arthritis, juvenile rheumatoid arthritis, and psoriasis. The term as used herein shall also mean the dosage of an antifolate which directly or indirectly reduces or increases the activity of molecules secreted by inflammatory and/or non-inflammatory cells participating in an inflammatory disorder in a human or mammal, such that the amount of antifolate arrests, reduces, or eliminates altogether the degree of pathologic inflammation associated with the inflammatory disorder. Typically, a therapeutically effective amount will also eliminate, reduce, or prevent the progression of, one or more disease manifestations. A skilled artisan readily recognizes that in many cases antifolates may not provide a cure, but may only provide partial benefit. Furthermore, the skilled artisan recognizes that because individual patients and disease states may vary, some patients may receive little, or no benefit at all. A dosage of antifolate that "kills", "arrests", "reduces" or "eliminates" as described above, in a least some patients, is considered therapeutically effective. The dose magnitude of a therapeutically effective amount of aminopterin in the acute or chronic management of a disorder will vary with the severity of the disorder to be treated and the route of administration. The dosage and dose rate of aminopterin will depend on a variety of factors, such as the weight and calculated surface area of the patient, the specific pharmaceutical composition used, the object of the treatment, i.e., therapy or prophylaxis, the nature of the disease to be treated, the judgment of the treating physician, and the response of the individual patient. In general, a therapeutically effective amount of aminopterin will be a dose of aminopterin from 0.1 mg/m$^2$ to about 4 mg/m$^2$, and typically a dose from 0.5 mg/m$^2$ to about 2 mg/m$^2$, given as a single or divided dose at a frequency ranging from about daily to weekly for a period ranging from several weeks to up to 30 months, or even longer. Patients may be upward titrated from below to within these dose ranges to a satisfactory control of disease manifestations. In some cases, it may be necessary to use dosages outside these ranges. For example, in some embodiments, dosages employing up to 500 mg/m$^2$ can be administered. Once improvement in the patient's condition has occurred, a maintenance dosage of a composition of this invention is administered, if necessary. Subsequently, the dose rate may be reduced by reducing the dose or frequency of administration, or a combination of both, as a function of the symptoms, to a level at which the improved condition is retained. When the symptoms have been alleviated to the desired level, the practitioner may elect to cease treatment. Patients may, however, require intermittent treatment upon any recurrence of disease symptoms, or prophylactically scheduled treatments as required. The therapeutically effective amount of aminopterin may optionally be administered prior to, contemporaneous with, or after at least one therapeutically effective dose of leucovorin or folic acid. For example, 5 mg/m$^2$ leucovorin may be administered twice at approximately 12 hour intervals beginning approximately 24 hours after the most recent dose of aminopterin. High doses of aminopterin up to 500 mg/m$^2$ will require that up to 50 mg/m$^2$ leucovorin be administered.

The term "toxicity component" as used herein refers to the dosage (i.e. dose and frequency of administration) required to produce a toxicity manifestation in a percentage of a population. An example of a commonly used toxicity component is the $TD_{50}$, which describes the dose in a particular dosage required to produce a toxicity manifestation in 50% of a population. Generally, there is an inverse relationship between dose and frequency necessary to produce the same toxicity component, where less antifolate given more often will produce the same toxicity component as more antifolate given less often.

The term "toxicity manifestation" as used herein refers to any undesired effect of a drug. A drug is said to be toxic or have toxicity if it causes a toxicity manifestation in a percentage of a population. For antifolates, particular toxicity manifestations include, but are not limited to mucositis, alopecia, diarrhea, myelosuppression, nephrotoxicity, hepatotoxicity, severe hepatotoxicity, neurotoxicity, and death. Toxicity manifestations also include indirect indications of toxicity such as thrombocytopenia (e.g. <50,000 µL), neutropenia (e.g. <750 µL), elevated liver enzymes (e.g. >5 time normal), erythrocyte antifolate (e.g. eAMT and eMTX), the necessary discontinuation of therapy by a patient because of the inability to endure further treatment with the drug, or increased hospital admissions due to the inability to continue therapy. Thus, a practitioner can assess the presence and the magnitude of a particular toxicity manifestation. Many, if not all, of the toxicity manifestations of antifolates can be reversed by the prior, contemporaneous or subsequent administration of leucovorin, a reduced folate that is well known in the art to rescue antifolate toxicity.

DETAILED DESCRIPTION OF THE INVENTION

Embodiments of the present invention provide compositions and methods for treating a patient with a therapeutically effective amount of aminopterin, or a pharmaceutically acceptable salt thereof, that provide better therapeutic benefits than methotrexate, where the therapeutic benefits include but are not limited to interpatient and intrapatient variability in oral bioavailability, therapeutic index, variability in toxicity, efficacy in combination therapy, and efficacy of certain polyglutamates.

Within certain embodiments, the present invention provides a method for treating a disorder in a pediatric patient with an antifolate having greater interpatient oral bioavailability than methotrexate, which comprises orally administering to said pediatric patient a therapeutically effective amount of aminopterin, or a pharmaceutically acceptable salt thereof. An embodiment of the present invention also provides a pharmaceutical composition comprising a therapeutically effective amount of aminopterin, or a pharmaceutically acceptable salt thereof, wherein the interpatient oral bioavailability of the aminopterin in a pediatric patient is greater than the interpatient oral bioavailability of methotrexate in a pediatric patient. In preferred embodiments, the aminopterin is the antifolate in an active pharmaceutical ingredient substantially free of impurities, or is the antifolate in an active pharmaceutical ingredient in a pharmaceutical composition substantially free of impurities. As defined herein, a pediatric patient is a human age 0 to 21 years.

In certain embodiments the interpatient oral bioavailability is greater than 60%, 70%, 80% and more preferably greater than 90%. In preferred embodiments, a dose of aminopterin from 0.1 mg/m$^2$ to about 4 mg/m$^2$ will have greater interpatient oral bioavailability than a 5- to 25-fold larger dose of methotrexate in the range of 1 mg/m² to about 100 mg/m 2. In a specific embodiment, an oral dose of 2 mg/m² of aminopterin provides an interpatient oral bioavailability of 94% in 27 matched pediatric patients. At approximately the equi-potent dose of 15-25 mg/m², the interpatient coefficient of variation of bioavailability of methotrexate in 22 matched pediatric patients was 59% [see Balis, et al., *Cancer Res.* 43(5):2342, 1983; Pinkerton, et al., *Br. J. Cancer* 45(2):300, 1982; and Pinkerton, et al., *Cancer Chemother. Pharmacol.* 10(1):36, 1982].

An embodiment of the present invention further provides methods of treating a disorder in a human with an antifolate having a smaller interpatient coefficient of variation of oral bioavailability than the interpatient coefficient of variation of oral bioavailability of methotrexate, which comprises orally administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the interpatient coefficient of variation of oral bioavailability is smaller than the interpatient coefficient of variation of oral bioavailability of methotrexate. In preferred embodiments, the aminopterin is the antifolate in an active pharmaceutical ingredient substantially free of impurities, or is the antifolate in an active pharmaceutical ingredient in a pharmaceutical composition substantially free of impurities.

In some embodiments, the interpatient coefficient of variation of oral bioavailability is less than 55%, and more preferably less than 45%. In preferred embodiments, a dose of aminopterin from 0.1 mg/m² to about 4 mg/m² will have a smaller interpatient coefficient of variation of oral bioavailability than a 5- to 25-fold larger dose of methotrexate in the range of 1 mg/m² to about 100 mg/m². In a specific embodiment, an oral dose of 2 mg/m² of aminopterin results in an interpatient coefficient of variation of oral bioavailability of 42%. At approximately the equi-potent dose of 15-25 mg/m², the interpatient coefficient of variation of bioavailability of methotrexate in 22 matched patients was 59% [see Balis, et al., *Cancer Res.* 43(5):2342, 1983; Pinkerton, et al., *Br. J. Cancer* 45(2):300, 1982; and Pinkerton, et al., *Cancer Chemother. Pharmacol.* 10(1):36, 1982].

An embodiment of the present invention further provides methods of treating a disorder in a human with an antifolate having a smaller mean intrapatient coefficient of variation of oral bioavailability than the mean intrapatient coefficient of variation of oral bioavailability of methotrexate, which comprises orally administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the mean intrapatient coefficient of variation of oral bioavailability is smaller than the mean intrapatient coefficient of variation of oral bioavailability of methotrexate. In preferred embodiments, the aminopterin is the antifolate in an active pharmaceutical ingredient substantially free of impurities, or is the antifolate in an active pharmaceutical ingredient in a pharmaceutical composition substantially free of impurities.

In some embodiments, the mean intrapatient coefficient of variation of oral bioavailability is less than 30%, and more preferably less than 25%. In preferred embodiments, a dose of aminopterin from 0.1 mg/m² to about 4 mg/m² will have a smaller mean intrapatient coefficient of variation of oral bioavailability than a 5- to 25-fold larger dose of methotrexate in the range of 1 mg/m² to about 100 mg/m². In a specific embodiment, an oral dose of 2 mg/m² of aminopterin results in a mean interpatient coefficient of variation of oral bioavailability of 25% in 5 patients. At approximately the equipotent dose of 15-25 mg/m², the mean intrapatient coefficient of variation of bioavailability of methotrexate was 34% in 38 patients [see Balis, et al., *Blood,* 92(10):3569, 1998].

Within further aspects, the present invention provides methods for treating a disorder in a human with an antifolate having an equivalent or greater therapeutic index than the corresponding therapeutic index of methotrexate, which comprises administering to said human a therapeutically effective amount of aminopterin, or a pharmaceutically acceptable salt thereof. An embodiment of the invention also provides for a pharmaceutical composition comprising a therapeutically effective amount of aminopterin, or a pharmaceutically acceptable salt thereof, wherein the therapeutic index is equal to or greater than the corresponding therapeutic index of methotrexate. The term "corresponding therapeutic index of methotrexate" means that the therapeutic indices of aminopterin and methotrexate are derived for the same disease manifestation and toxicity manifestation (see glossary). In preferred embodiments, the aminopterin is the antifolate in an active pharmaceutical ingredient substantially free of impurities, or is the antifolate in an active pharmaceutical ingredient in a pharmaceutical composition substantially free of impurities.

In some embodiments, the therapeutic index of aminopterin is equal to or greater than 1-fold, 5-fold, 10-fold, 50-fold, and more preferably equal to or greater than 100-fold the therapeutic index of methotrexate. In preferred embodiments, a dose of aminopterin from 0.1 mg/m² to about 4 mg/m² will have an equal or greater therapeutic index than a 5- to 25-fold larger dose of methotrexate in the range of 1 mg/m² to about 100 mg/m².

In a specific embodiment of a therapeutic index derived for peripheral blasts in T-lineage acute lymphoblastic leukemia (disease manifestation) and mucositis (toxicity manifestation), a divided oral dose of 4 mg/m² of aminopterin results in a therapeutic index of 1, while a dose of greater than 5,000 mg/m² methotrexate results in a relative therapeutic index of <0.02. The therapeutic index of aminopterin in this embodiment is therefore greater than 50-fold the corresponding therapeutic index of methotrexate.

In other specific embodiments, one or more oral doses of 4 mg/m² of aminopterin and 100 mg/m² of methotrexate results in equal therapeutic indices, wherein the therapeutic indices are derived for peripheral blasts in acute lymphoblastic leukemia (disease manifestation) and a variety of toxicity manifestations that can include, for example, mucositis, neutropenia, thrombocytopenia, myelosuppression, hospital admissions, treatment interruptions, elevation in liver enzymes, and erythrocyte antifolate. In contrast, the prior art teaches that aminopterin has a smaller therapeutic index than methotrexate [see Burchenal et al., *Cancer* 2:113, 1949; Farber et al., *Advances in Cancer research,* pp 2-73. New York: Academic Press, 1956; Dacie et al., *B.M.J.* 1: 1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979].

An embodiment of the present invention further provides methods of treating a disorder in a human with an antifolate having an equivalent or smaller coefficient of variation of toxicity than the corresponding coefficient of variation of toxicity of methotrexate, which comprises administering to said human a therapeutically effective amount of aminopterin, or a pharmaceutically acceptable salt thereof. Also provided are pharmaceutical compositions comprising a therapeutically effective amount of aminopterin, or a pharmaceutically acceptable salt thereof, wherein the coefficient of variation of toxicity is equal to or smaller than the corresponding coefficient of variation of toxicity of methotrexate. The term "corresponding coefficient of variation of toxicity of methotrexate" means that the coefficient of variation of aminopterin and methotrexate are derived for the same toxicity manifestation (see glossary). In preferred embodiments, the aminopterin is the antifolate in an active pharmaceutical ingredient substantially free of impurities, or is the antifolate in an active pharmaceutical ingredient in a pharmaceutical composition substantially free of impurities.

In some embodiments, the coefficient of variation of toxicity of aminopterin is less than or equal to 100%, 75%, 50%, and more preferably less than or equal to 20% of the corresponding coefficient of variation of toxicity of methotrexate. In preferred embodiments, one or more doses of aminopterin from 0.1 mg/m$^2$ to about 4 mg/m$^2$ will have a smaller coefficient of variation of toxicity than one or more 5- to 250-fold larger doses of methotrexate in the range of 1 mg/m$^2$ to about 1000 mg/m$^2$. In a specific embodiment, the coefficient of variation of erythrocyte antifolate levels (toxicity manifestation) was calculated to be 67% and 538% for 2 mg/m$^2$ aminopterin and 20 mg/m$^2$ methotrexate both given orally, respectively. Thus, the coefficient of variation of toxicity of aminopterin was 12.4% the corresponding coefficient of variation of toxicity of methotrexate.

In another specific embodiment, the coefficient of variation of elevated liver enzymes (toxicity manifestation) was calculated to be 25% and 36% for 2 mg/m$^2$ aminopterin and 25 mg/m$^2$ methotrexate both given orally, respectively. The coefficient of variation of toxicity of aminopterin was 71% the corresponding coefficient of variation of toxicity of methotrexate. In contrast, the prior art teaches that the toxicity of aminopterin is more variable than the toxicity of methotrexate [see Burchenal et al., *Cancer* 2:113, 1949; Farber et al., *Advances in Cancer research*, pp 2-73. New York: Academic Press, 1956; Dacie et al., *B.M.J.* 1: 1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979].

Embodiments of the present invention further provide methods for treating a disorder in a patient using combination therapy, which comprises administering to said patient a therapeutically effective amount of aminopterin, or a pharmaceutically acceptable salt thereof, according to a therapeutic protocol involving at least one other therapeutic. The at least one other therapeutic may be administered prior to, contemporaneous with, or after administering the aminopterin. The at least one other therapeutic also includes a single dosage form containing aminopterin and at least one other therapeutic, a multiple dosage form, wherein the aminopterin and the at least one other therapeutic are administered separately, but concurrently, or a multiple dosage form wherein the two components are administered separately, but sequentially. The at least one other therapeutic can be, for example, folic acid, leucovorin, dextromethorphan, memantine, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluoruracil, dianydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, antibodies, and humanized antibodies.

In preferred embodiments, a dose of aminopterin from 0.1 mg/m$^2$ to about 4 mg/m$^2$ is suitable for use in a therapeutic protocol employed during a combination therapy. In preferred embodiments, the aminopterin is the antifolate in an active pharmaceutical ingredient substantially free of impurities, or is the antifolate in an active pharmaceutical ingredient in a pharmaceutical composition substantially free of impurities. In some embodiments, aminopterin can be directly substituted for methotrexate in a therapeutic protocol employing methotrexate by administering aminopterin at about 4-8% of the dose of methotrexate in the protocol. In specific embodiments, aminopterin is substituted for methotrexate in the consolidation and intensive continuation phases of the therapeutic protocol for treating ALL by administering two oral doses of 2 mg/m$^2$ aminopterin instead of four oral doses of 25 mg/m$^2$ methotrexate. This substitution yields the same level of efficacy and therapeutic index as methotrexate, but with at least 10-fold fewer tablets taken by the patient. In another specific embodiment, aminopterin is substituted for methotrexate in the treatment of juvenile or adult rheumatoid arthritis in a therapeutic protocol employing another non-steroidal anti-inflammatory drug by administering a single weekly oral dose of 0.5 to 2 mg aminopterin instead of a single weekly dose of 7-25 mg methotrexate. In another specific embodiment, psoriasis in an adult is treated in a therapeutic protocol in week 1 with 0.5 mg/day aminopterin, in week 2 with no treatment, in week 3 with 0.5 mg/day aminopterin, and in weeks 4 and 5 with 0.5 mg aminopterin every other day.

In contrast, the prior art only teaches the clinical use of aminopterin only as a single agent in the 1940s and 1950s for the treatment of acute leukemia, psoriasis and arthritis in humans, and teaches that methotrexate has a better therapeutic index and less variable toxicity [see Farber et al., *N. Engl. J. Med.* 238:787, 1948; Gubner, *Arch. Derm., Chicago* 64:688, 1951; Rees et al., *Arch. Derm., Chicago* 90:544, 1964; Gubner et al., *Am. J. Med. Sci.* 22:176, 1951; Burchenal et al., *Cancer* 2:113, 1949; Farber et al., *Advances in Cancer research*, pp 2-73. New York: Academic Press, 1956; Dacie et al., *B.M.J.* 1:1447, 1950; Sacks, et al., *Ann. Intern. Med.* 32:80, 1950; Goldin et al., *J. Natl. Cancer Inst.* 5:1657, 1955; and Glode et al., *Cancer Res.* 39:3707, 1979]. Such a single use approach to treatment was abandoned and the use of aminopterin in combination therapy using a therapeutic protocol has never been reported in the last 60 years.

An embodiment of the present invention further provides methods for treating a disorder in a human with the antifolate aminopterin that is metabolized to a polyglutamate having a different relative frequency than the relative frequency of the corresponding methotrexate polyglutamate, which comprises administering to said human a therapeutically effective amount of aminopterin, or a pharmaceutically acceptable salt thereof (see glossary for the definition of "relative frequency"). Also provided are pharmaceutical compositions comprising a therapeutically effective amount of aminopterin, or a pharmaceutically acceptable salt thereof, wherein the aminopterin is metabolized to a polyglutamate having a different relative frequency than the relative frequency of the corresponding methotrexate polyglutamate. The phrase "corresponding methotrexate polyglutamate" as used herein means the methotrexate polyglutamate whose chain length corresponds to the aminopterin polyglutamate with the same chain length.

The relative frequency of two polyglutamates is said to be different if the relative frequency of one polyglutamate is greater than 10%, 20%, and more preferably greater than 30%, the relative frequency of the other polyglutamate. In some embodiments, aminopterin is metabolized to two, three and more preferably four or more polyglutamates each having a different relative frequency than the relative frequency of the corresponding methotrexate polyglutamates. For example, the relative frequencies in a mixture of aminopterin-(glu)$_n$ species obtained from a patient's leukemic cells may consist of 5% (n=1), 70% (n=2), 15% (n=3), 5% (n=4) and 5% (n=5). The relative frequencies from a mixture of methotrexate-(glu)$_n$ species obtained from the same patient's leukemic cells may consist of 25% (n=1), 10% (n=2), 15% (n=3), 35% (n=4) and 15% (n=5). In this example, the relative frequencies of the corresponding polyglutamates are said to be different for n=2 (differs by 60%), 4 (differs by 30%) and 5 (differs by 10%), while n=1 is not a polyglutamate.

In still other embodiments, aminopterin polyglutamates will have a smaller weighted average chain length than the weighted average chain length of the corresponding methotrexate polyglutamates. The weighted average chain length is calculated by multiplying each relative frequency (expressed as a fraction) by its respective n for each polyglutamate and the free antifolate, and summing the products. If the relative frequencies are expressed as a percent, the sum is divided by 100. For example, the relative frequencies in a mixture of aminopterin-(glu)$_n$ species obtained from a patient's leukemic cells consisting of 5% (n=1), 70% (n=2), 15% (n=3), 5% (n=4) and 5% (n=5) provide a weighted average chain length of (5×1)+(70×2)+(15×3)+(5×4)+(5×5)/100=2.35. By comparison, the relative frequencies from a mixture of methotrexate-(glu)$_n$ species obtained from the same patient's leukemic cells consisting of 25% (n=1), 10% (n=2), 15% (n=3), 35% (n=4) and 15% (n=5) provide a larger weighted average chain length of 2.75. In other embodiments, the aminopterin polyglutamate having a total of two attached glutamates is the majority polyglutamate.

In preferred embodiments, a dose of aminopterin from 0.1 mg/m$^2$ to about 4 mg/m$^2$ is metabolized to a polyglutamate having a different relative frequency than the relative frequency of the corresponding methotrexate polyglutamate obtained from a dose of methotrexate in the range of 1 mg/m$^2$ to about 1000 mg/m$^2$. In some embodiments, aminopterin and its polyglutamated metabolites together have a maximum level of efficacy equal to or greater than the maximum level of efficacy of methotrexate together with its polyglutamated metabolites. In other embodiments, the aminopterin and its polyglutamated metabolites together have a therapeutic index equal to or greater than the therapeutic index of methotrexate together with its polyglutamated metabolites. Thus, aminopterin and its particular pattern of relative frequencies of polyglutamates has unexpected clinical advantages. Although the disclosed invention is not to be limited by theory, this may possibly be due to a uniquely advantageous intracellular distribution of shorter chain polyglutamates to particular intracellular targets that are not as easily accessed by longer chain polyglutamates. In preferred embodiments, the aminopterin is the antifolate in an active pharmaceutical ingredient substantially free of impurities, or is the antifolate in an active pharmaceutical ingredient in a pharmaceutical composition substantially free of impurities.

An embodiment of the present invention further provides methods of treating a disorder in a human, which comprises administering to said human an active pharmaceutical ingredient substantially free of impurities, wherein the antifolate in the active pharmaceutical ingredient is a therapeutically effective amount of aminopterin, or a pharmaceutically acceptable salt thereof. In some embodiments, the impurities may include, for example, folic acid, pterins, and conjugates of p-aminobenzoic acid. In preferred embodiments, the aminopterin purity in the active pharmaceutical ingredient is equal to or greater than 95 area %, equal to or greater than 95 weight %, or equal to or greater than 95 mole % (see "aminopterin purity" in glossary). In other embodiments, the active pharmaceutical ingredient has less than 5 area %, less than 5 weight %, or less than mole % impurities, and more preferably less than 3 area %, less than 3 weight %, or less than 3 mole % impurities. In preferred embodiments, administering an active pharmaceutical ingredient containing an aminopterin dose from 0.1 mg/m$^2$ to about 4 mg/m$^2$ will provide a therapeutically effective amount of aminopterin and will be substantially free of impurities.

The chemical synthesis of an active pharmaceutical ingredient substantially free of impurities and containing aminopterin can be performed by several different sequences of organic synthetic steps. It is understood that one or ordinary skill in the art would be able to make an active pharmaceutical ingredient substantially free of impurities and containing aminopterin in light of the following disclosure, including the Examples, and information known to those of ordinary skill in the chemical synthesis field. For example, beginning with readily available starting materials, an active pharmaceutical ingredient substantially free of impurities and containing aminopterin may be synthesized according to the following reaction scheme.

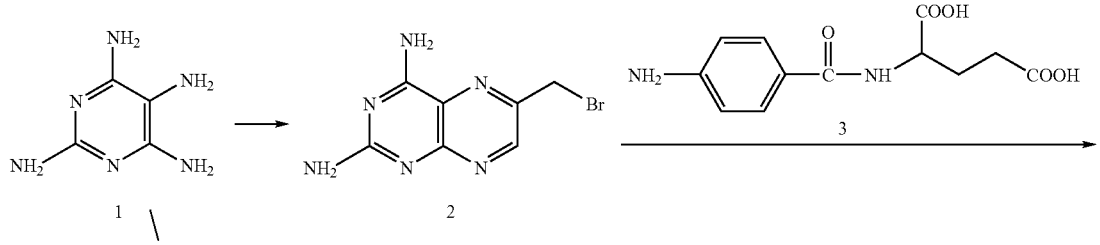

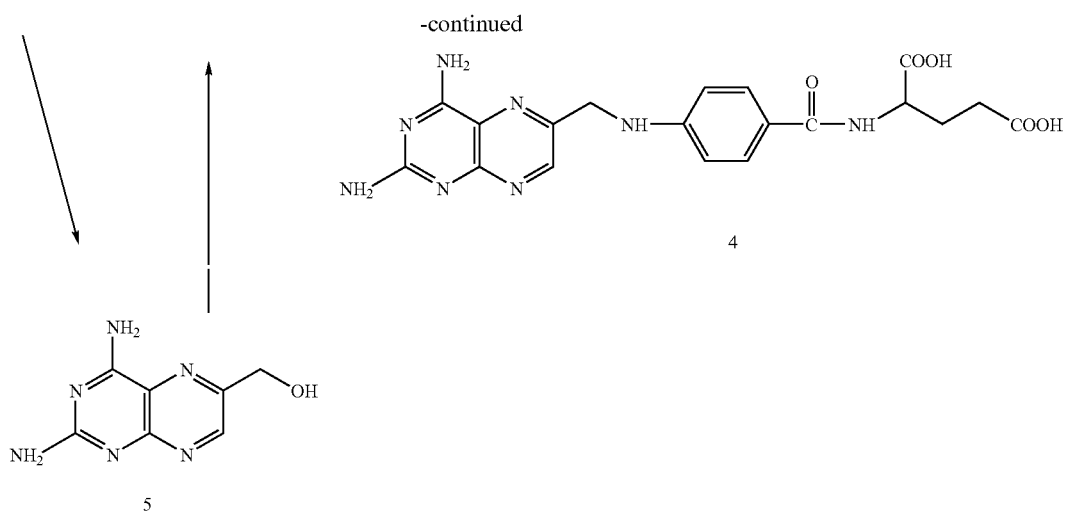

As illustrated in the reaction scheme, the commercially available 2,4,5,6-tetraminopyrimidine, compound 1, may be condensed with β-bromopyruvaldoxime to provide 2,4-diamino-6-(bromomethyl)pteridine, compound 2 [see Taghavi-Moghadam and Pfleiderer, *Tet. Lett.* 38:6835, 1997 and Taylor and Portnoy, *J. Org Chem.* 38:806, 1973]. Alternatively, compound 1 may be reacted with 1,3-dihydroxyacetone to provide 2,4-diamino-6-pteridinemethanol, compound 5 [see Baugh and Shaw, *J. Org Chem.* 29:3610, 1964]. Compound 5 is purified and reacted with HBr and dibromotriphenylphosphorane ($Ph_3PBr_2$) in dimethylacetamide to afford compound 2 [see Piper and Montgomery, *J. Org. Chem.* 42:208, 1977; Piper and Montgomery, *J. Heterocycl. Chem.* 11:279, 1974; Piper and Montgomery, U.S. Pat. No. 4,077,957; and Piper and Montgomery, U.S. Pat. No. 4,079,056]. In still other embodiments, compound 2 can be arrived at via the reaction of compound 1 with 1,1-dichloroacetone to form 2,4-diamino-6-(methyl)pteridine, which is then reacted with bromide [see Catalucci, U.S. Pat. No. 4,224,446].

Regardless of the route to its synthesis, compound 2 is condensed with commercially available N-(p-aminobenzoyl)-L-glutamic acid, compound 3, in dimethylacetamide to afford the active pharmaceutical ingredient substantially free of impurities and containing aminopterin, compound 4, as the antifolate [see Piper and Montgomery, *J. Org Chem.* 42:208, 1977; Piper and Montgomery, U.S. Pat. No. 4,077,957; Piper and Montgomery, U.S. Pat. No. 4,079,056; and Catalucci, U.S. Pat. No. 4,224,446].

In other embodiments, an active pharmaceutical ingredient substantially free of impurities and containing aminopterin as the antifolate may be obtained by purification of aminopterin preparations contaminated with impurities by, for example, ion-exchange chromatography or by HPLC [see Heinrich et al., *J. Am. Chem. Soc.* 75:5425, 1953 and Tong et al., *Lancet* 2:719, 1975]. In still other embodiments, an active pharmaceutical ingredient substantially free of impurities and containing aminopterin as the antifolate may be obtained by the direct transformation (i.e. amination) of folic acid to aminopterin and subsequent purification by HPLC [see Zimmermann, U.S. Pat. No. 4,767,859].

An embodiment of the present invention further provides pharmaceutical compositions substantially free of impurities and comprising an active pharmaceutical ingredient, wherein the antifolate in the active pharmaceutical ingredient is a therapeutically effective amount of aminopterin, or a pharmaceutically acceptable salt thereof. In some embodiments, the impurities may include, for example, folic acid, pterins, and conjugates of p-aminobenzoic acid. In preferred embodiments, the pharmaceutical composition has less than 5 area %, less than 5 weight %, or less than 5 mole % impurities, and more preferably less than 3 area %, less than 3 weight %, or less than 3 mole % impurities. In other embodiments, the aminopterin purity in the pharmaceutical composition is equal to or greater than 95 area %, equal to or greater than 95 weight %, or equal to or greater than 95 mole %. In preferred embodiments, a pharmaceutical composition containing from 0.2 mg to about 2.0 mg aminopterin will provide a therapeutically effective amount of aminopterin and will be substantially free of impurities.

The aminopterin purity of the active pharmaceutical ingredient is used to established how much active pharmaceutical ingredient is required in the pharmaceutical composition to obtained a desired final dose of aminopterin, or a pharmaceutically acceptable salt thereof, in the pharmaceutical composition. For example, if a pharmaceutical composition is to contain about 1 mg of aminopterin and the aminopterin purity in the active pharmaceutical ingredient is 95 weight %, then about 1.0526 mg of the active pharmaceutical ingredient will be required in the pharmaceutical composition to provide about 1 mg of aminopterin.

In addition to the active pharmaceutical ingredient, pharmaceutical compositions substantially free of impurities contain one or more pharmaceutically acceptable carriers (see glossary definition of "pharmaceutical composition"). Pharmaceutical compositions substantially free of impurities are most readily prepared by combining an active pharmaceutical ingredient substantially free of impurities, wherein aminopterin is the antifolate in the active pharmaceutical ingredient, in intimate admixture with one or more pharmaceutical carriers according to conventional pharmaceutical compounding techniques.

The carrier may take a wide variety of forms depending on the form of the pharmaceutical composition (i.e. "preparation" or "form") desired for administration, e.g., oral or parenteral (including intravenous injections or infusions). In preparing the pharmaceutical composition in an oral dosage form any of the usual pharmaceutical carriers may be employed. Usual pharmaceutical carriers include, for example, water, glycols, oils, alcohols, flavoring agents, preservatives, coloring agents, and the like in the case of oral liquid preparations (such as for example, suspensions, solutions, and elixirs); aerosols; or carriers such as starches, sugars (e.g. lactose), microcrystalline cellulose, diluents, granulating agents, lubricants, binders, disintegrating agents and the like, in the case of oral solid preparations (such as for example, powders, capsules, and tablets) with the oral solid preparations generally being preferred over the oral liquid preparations. For pediatric patients, however, it will be appreciated to those skilled in the art that pleasant tasting oral liquid preparations are preferred.

Because of their ease of administration, tablets and capsules represent the most advantageous oral dosage form in adults, in which case solid pharmaceutical carriers are employed. If desired, tablets may be coated by standard aqueous or nonaqueous techniques. The parenteral dosage form can consist of a sterile solution of the active ingredient, either in its free or salt form, in physiological buffer or sterile water. In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field. In embodiments employing parenteral, oral liquid, or other aqueous compositions, care must be taken since electrophilic substitution by water converts aminopterin to folic acid, and such preparations have been noted to accumulate folic acid to undesirable levels over the course of six months of storage. Accordingly, such aqueous compositions are best stored desiccated and hydrated within several hours to several days prior to patient administration.

In addition to the common dosage forms set out above, the pharmaceutical compositions of the present invention may also be administered by controlled release means and/or delivery devices such as those described in U.S. Pat. Nos. 3,845,770; 3,916,899; 3,536,809; 3,598,123; 3,630,200; 4,008,719; 4,687,660 and 4,769,207, the disclosures of which are hereby incorporated by reference.

Optionally, the pharmaceutical composition contains other therapeutic ingredients. Such therapeutic ingredients may be added to ameliorate certain side-effects, particularly those of aminopterin, or add to patient convenience by reducing the number of dosage forms that must be taken. Suitable therapeutic ingredients for combining with the pharmaceutical composition may include, for example, folic acid, leucovorin, dextromethorphan, memantine, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluoruracil, dianydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, antibodies, and humanized antibodies.

As used in the methods and compositions of the present disclosure, the term "pharmaceutically acceptable salts" refers to salts prepared from pharmaceutically acceptable non-toxic acids or bases including inorganic acids and bases and organic acids and bases. The sodium or di-sodium salts of aminopterin are pharmaceutically acceptable salts of aminopterin.

Since aminopterin is both basic and acidic, salts may be prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like. Such salts may also contain the following cations: aluminum, calcium, lithium, magnesium, potassium, sodium, zinc, benzathine, chloroprocaine, choline, diethanolamine, ethylenediamine, meglumine, and procaine.

Unless the route of administration is specified in a method disclosed herein, any suitable route of administration may be employed for providing a human with a therapeutically effective amount of aminopterin, or a pharmaceutically acceptable salt thereof. For example, oral, rectal, parenteral, transdermal, subcutaneous, intramuscular, and the like may be employed as appropriate. Dosage forms include tablets, coated tablets, troches, dispersions, suspensions, solutions, caplets, capsules, patches, and, the like. Pharmaceutical compositions include those suitable for oral, rectal and parenteral (including subcutaneous, intramuscular, and intravenous) administration, although the most suitable route in any given case will depend on the nature and severity of the disorder being treated. The most preferred route of the present invention is the oral route. The pharmaceutical compositions may be conveniently presented in unit dosage form, and prepared by any of the methods well known in the art of pharmacy.

Pharmaceutical compositions of the present invention suitable for oral administration may be presented as discrete units such as capsules, cachets, or tablets, or aerosols sprays, each containing a predetermined amount of the pharmaceutically active ingredient, as a powder or granules, or as a solution or a suspension in an aqueous liquid, a non-aqueous liquid, an oil-in-water emulsion, or a water-in oil liquid emulsion. Such pharmaceutical compositions may be prepared by any of the methods of pharmacy, but all methods include the step of bringing into association the active pharmaceutical ingredient with at least one pharmaceutical carrier. In general, the pharmaceutical compositions are prepared by uniformly and intimately admixing the active pharmaceutical ingredient with liquid pharmaceutical carriers or finely divided solid pharmaceutical carriers or both, and then, if necessary, shaping the product into the desired presentation.

For example, a tablet may be prepared by compression or molding, optionally, with one or more accessory ingredients. Compressed tablets may be prepared by compressing in a suitable machine the active pharmaceutical ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 0.5 mg to about 2 mg of aminopterin or a therapeutically acceptable salt thereof, and each cachet or capsule contains from about 0.5 mg to about 2 mg of aminopterin or a therapeutically acceptable salt thereof. Most preferably, the tablet, cachet or capsule contains either one of two dosages, about 0.5 mg or about 1 mg of aminopterin or a therapeutically acceptable salt thereof.

In still other embodiments, pharmaceutical compositions contain a therapeutically effective amount of aminopterin, or a therapeutically acceptable salt thereof, with a standard deviation of less than 5%, and more preferably a standard deviation of less than 3%. The standard deviation is a measure of dose uniformity (i.e. consistency) in the pharmaceutical compositions with a smaller standard deviation being an indication of greater dose uniformity. The pharmaceutical compositions may be different portions of a single pharmaceutical composition from a single formulation batch, or may be from multiple pharmaceutical compositions of the same dosage form that are each the result of different formulation batches. Thus, the standard deviation can be a measure of dose uniformity both within the same batch and between batches.

The standard deviation of an antifolate in pharmaceutical compositions is determined by measuring the amount of antifolate in a known amount of each pharmaceutical composition using methods familiar to those in the art. For example, the amount of aminopterin and methotrexate in a pharmaceutical composition can be quantitated using scanning UV spectrophotometry, HPLC, or a radioligand DHFR binding assay [see Kamen et al., *Anal. Biochem.* 70:54, 1976 and Ratliff et al., *J. Clin. One.* 16:1458, 1998]. As defined herein, calculation of a standard deviation requires measuring aminopterin from at least two randomly selected parts of a single batch of a pharmaceutical composition, or from each of at least two different batches of a pharmaceutical composition.

The invention is further defined by reference to the following examples describing in detail, the methods, and use and preparation of the pharmaceutical compositions of the present invention. It will be apparent to those skilled in the art, that many modifications, both to materials, and methods, may be practiced without departing from the purpose and interest of this invention.

EXAMPLES

In Examples 1-49 that follow, "aminopterin" is the antifolate in an active pharmaceutical ingredient employed in a pharmaceutical composition substantially free of impurities. In the majority of the examples, the pharmaceutical composition was a tablet form, but occasionally a liquid form was used. The impurities in Examples 60 and 61 were typical of the impurities in the aminopterin and pharmaceutical compositions in Examples 1-55, 59, and 66.

Example 1

Interpatient Oral Bioavailability

Pharmacokinetic studies of aminopterin were performed in pediatric patients (age 0-21) using a 2 mg/m$^2$ dose where the AUC was determined for intravenous and oral routes of administration of the same dose in each patient (i.e. matched values). The interpatient oral bioavailability in 15 matched pediatric patients was 94% (see Table I). The prior art indicates that at the same dose, the interpatient oral bioavailability in 13 matched adult patients was only 85% [see Ratliff et al., *J. Clin. One.* 16:1458, 1998]. The prior art further indicates that at approximately the equipotent dose of 15-25 mg/m$^2$, the interpatient oral bioavailability of methotrexate in 22 matched pediatric patients was 44% [see Balis, et al., *Cancer Res.* 43(5):2342, 1983; Pinkerton, et al., *Br. J. Cancer* 45(2): 300, 1982; and Pinkerton, et al., *Cancer Chemother. Pharmacol.* 10(1):36, 1982].

Examples 2-3

Interpatient Coefficient of Variation of Oral Bioavailability

Pharmacokinetic studies of aminopterin were performed in pediatric and adult patients using a 2 mg/m$^2$ dose where the AUC was compared for intravenous and oral routes of delivery in each patient. The standard deviation of oral bioavailability and interpatient oral bioavailability were determined among 27 matched patients. The interpatient coefficient of variation of oral bioavailability was calculated to be 42% by dividing the standard deviation by the interpatient oral bioavailability and expressing it as a percent (see Table II).

The prior art indicates that at approximately the equipotent dose of 15-25 mg/m$^2$, the interpatient coefficient of variation of bioavailability of methotrexate in 22 matched patients was 59% [see Balis, et al., *Cancer Res.* 43(5):2342, 1983; Pinkerton, et al., *Br. J. Cancer* 45(2):300, 1982; and Pinkerton, et al., *Cancer Chemother. Pharmacol.* 10(1):36, 1982].

Examples 4-5

Mean Intrapatient Coefficient of Variation of Oral Bioavailability

Pharmacokinetic studies of aminopterin were performed in the same patient using consecutive paired 2 mg/m$^2$ oral and intravenous dosings given days to weeks apart from one another, whereby multiple determinations of oral bioavailability were made in the same patient. The intrapatient oral bioavailability and standard deviation of the oral bioavailability were determined among the consecutive doses in a given patient, and the intrapatient coefficient of variation of oral bioavailability calculated for each patient by dividing the standard deviation by the intrapatient oral bioavailability. This was repeated in 5 patients, and the mean intrapatient coefficient of variation of oral bioavailability determined among the 5 patients to be 25% (see Table III).

Using an identical algorithm for calculating the mean intrapatient coefficient of variation of oral bioavailability, the prior art indicates that at approximately the equi-potent dose of 15-25 mg/m$^2$, that the intrapatient coefficient of variation of bioavailability of methotrexate among 38 patients was 34% [see Balis, et al., *Blood,* 92(10):3569, 1998].

Examples 6-31

Therapeutic Index

The prior art teaches that aminopterin has a smaller therapeutic index than methotrexate [see Burchenal et al., *Cancer* 2:113, 1949; Farber et al., *Advances in Cancer research*, pp 2-73. New York: Academic Press, 1956; Dacie et al., *B.M.J.* 1:1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979]. However, we have discovered that in human clinical trials comparing orally administered aminopterin and methotrexate tablets, that aminopterin has an equivalent or larger therapeutic index than methotrexate (Examples 6-31).

Specifically, a clinical trial was performed in human adult and pediatric patients having T-lineage acute lymphoblastic leukemia (ALL) that was refractory to therapy or that had relapsed (see Table IV). The disease manifestations that were monitored were peripheral blasts and bone marrow infiltrates. The toxicity manifestations that were monitored were mucositis, neutropenia, thrombocytopenia and myelosuppression. The methotrexate therapeutic component was >5,000 mg/m$^2$/wk, since there was no efficacy below this dose. The aminopterin therapeutic component was 4 mg/m$^2$/wk, which resulted in 43% of patients going into complete remission or stable disease. For each toxicity manifestation, an equivalent toxicity component was obtained for 4 mg/m$^2$/wk aminopterin and 100 mg/m$^2$/wk methotrexate. The therapeutic index for each paired therapeutic and toxicity component were calculated as their ratio, and in each case the therapeutic index was found to be larger for aminopterin than for methotrexate (Examples 6-13, Table IV).

In a further set of examples, a clinical trial was performed in adult and pediatric patients having standard and high-risk ALL (see Table V). The disease manifestations that were monitored were peripheral blasts and bone marrow infiltrates. The toxicity manifestations that were monitored were mucositis, neutropenia, thrombocytopenia, myelosuppression, hospital admissions, treatment interruptions, erythrocyte antifolate (eAMT and eMTX, indicators of bone marrow toxicity), and any elevation in liver enzymes. After 12 months of treatment, equivalent therapeutic components were obtained for 4 mg/m$^2$/wk aminopterin and 100 mg/m$^2$/wk methotrexate with both exhibiting no evidence of a disease manifestation in 100% of the patients. Equivalent toxicity components were obtained for each of the above toxicity manifestations at 4 mg/m$^2$/wk aminopterin and 100 mg/m$^2$/wk methotrexate. The therapeutic index for each paired therapeutic and toxicity component could therefore be calculated as their ratio, and in each case the therapeutic index was found to be equivalent for aminopterin and for methotrexate (Examples 14-29, Table V).

In a final set of examples comparing the therapeutic index of aminopterin and methotrexate, the patients from the high-risk ALL clinical trial were further examined for severe hepatotoxicity, a toxicity manifestation defined herein as liver enzyme elevations greater than five times normal (Table VI). As before, the disease manifestations that were monitored were peripheral blasts and bone marrow infiltrates, which after 12 months of treatment yielded equivalent therapeutic components for 4 mg/m 2/wk aminopterin and 100 mg/m$^2$/wk methotrexate. At 4 mg/m$^2$/wk aminopterin, severe hepatotoxicity was seen in 5.8% of patients. In contrast, 100 mg/m$^2$/wk methotrexate produced severe hepatotoxicity in 11.1% of patients. Thus, whereas 100 mg/m$^2$ of methotrexate and 4 mg/m$^2$ of aminopterin produce equivalent therapeutic manifestations, less than 100 mg/m$^2$ methotrexate would be required to produce an equivalent toxicity manifestation as 4 mg/m$^2$ aminopterin. The therapeutic indices of aminopterin relating peripheral blasts or bone marrow infiltration to severe hepatotoxicity are larger for aminopterin than for methotrexate (Examples 30-31, Table VI).

Examples 32-43

Coefficient of Variation of Toxicity

The prior art teaches that the toxicity of aminopterin is more variable than the toxicity of methotrexate and therefore more difficult to control [see Burchenal et al., *Cancer* 2:113, 1949; Farber et al., *Advances in Cancer research*, pp 2-73. New York: Academic Press, 1956; Dacie et al., *B.M.J.* 1: 1447, 1950; Sacks, M. S. et al., *Ann. Intern. Med.* 32:80, 1950; Goldin et al., *J. Natl. Cancer Inst.* 5:1657, 1955; and Glode et al., *Cancer Res.* 39:3707, 1979]. However, we have discovered that in human clinical trials comparing orally administered aminopterin and methotrexate tablets, that aminopterin has an equivalent or smaller coefficient of variation (i.e. relative variability) of toxicity than methotrexate (Examples 32-43).

A clinical trial was performed in adult and pediatric patients having standard and high-risk ALL (see Table VII). The toxicity manifestations that were monitored were level of liver enzymes above normal, erythrocyte antifolate (eAMT and eMTX, indicators of bone marrow toxicity), absolute neutrophil count in the consolidation phase of therapy and platelet counts in the consolidation phase of therapy. After 12 months of treatment, equivalent therapeutic components were obtained for 4 mg/m$^2$/wk aminopterin and 100 mg/m$^2$/wk methotrexate with both exhibiting no evidence of a disease manifestation in 100% of the patients. Equivalent toxicity components were obtained for each of the above toxicity manifestations at 4 mg/m$^2$/wk aminopterin and 100 mg/m$^2$/wk methotrexate. In each case the coefficient of variation of the toxicity manifestation was found to be equivalent or smaller for aminopterin than for methotrexate (Examples 32-43, Table VII).

Examples 44-49

Use in Combination Therapy

Twenty patients with high risk ALL were treated with aminopterin using a combination therapy protocol comprising consolidation, intensive continuation and continuation phases (Examples 45, 47 and 49; Tables VIII, IX and X). Twenty patients with standard risk ALL were treated with methotrexate using the same combination therapy protocol (Examples 44, 46 and 48; Tables VIII, IX and X). Compared to standard risk patients, high risk patients have a worse prognosis. Standard risk patients are those who at diagnosis are: 1 to less than 10 years of age, have a peripheral white blood cell count of less than 50,000 per microliter, no central nervous system disease and no testicular involvement. High risk patients are those who at diagnosis are: 10 years of age or older, have a peripheral white blood cell count of 50,000 per microliter or more, have central nervous system disease, have testicular involvement, or chromosomal translocations t(1; 19), t(4;11) or t(9;22). Despite the worse prognosis of the high risk patients treated with aminopterin, these patients had an equivalent survival rate to the standard risk patients treated with an equipotent dose of methotrexate during a follow-up period of up to 15 months. However, the patients (many pediatric) required at least 10-fold fewer tablets during each week of therapy, which was a major advantage in terms of patient compliance and convenience.

In contrast, the prior art only teaches the clinical use of aminopterin only as a single agent in the 1940s and 1950s for the treatment of acute leukemia, psoriasis and arthritis in humans, and teaches that methotrexate has a better therapeutic index and less variable toxicity [see Farber et al., *N. Engl. J. Med.* 238:787, 1948; Gubner, *Arch. Derm., Chicago* 64:688, 1951; Rees et al., *Arch. Derm., Chicago* 90:544, 1964; Gubner et al., *Am. J. Med Sci.* 22:176, 1951; Burchenal et al., *Cancer* 2:113, 1949; Farber et al., *Advances in Cancer research*, pp 2-73. New York: Academic Press, 1956; Dacie et al., *B.M.J.* 1:1447, 1950; Sacks, et al., *Ann. Intern. Med.* 32:80, 1950; Goldin et al., *J. Natl. Cancer Inst.* 5:1657, 1955; and Glode et al., *Cancer Res.* 39:3707, 1979]. The use of aminopterin in combination therapy has never been reported in the last 60 years.

Examples 50-55

Metabolism to Polyglutamates

Bone marrow leukemic blasts isolated from patients at initial diagnosis were incubated with 1 µM [$^3$H]-methotrexate or 0.1 µM [$^3$H]-aminopterin in vitro, representing the typical plasma concentrations in patients receiving the equipotent dose of 25 mg/m$^2$ methotrexate or 2 mg/m$^2$ aminopterin, respectively. After 24 h, the cells were collected, washed, and lysed. Antifolyl-polyglutamates were separated by HPLC and compared to known, unlabeled standards (see Table XI). In lymphoblasts from patients with B-lineage ALL, methotrexate polyglutamates from (glu)$_2$ through (glu)$_5$ are found in increasing frequency with increasing chain length, while the corresponding aminopterin polyglutamates are found in decreasing frequency (compare Examples 50 and 51). The pattern of aminopterin polyglutamates in T-ALL or AML blasts also differs dramatically from that seen in blasts treated with methotrexate, where aminopterin-(glu)$_2$ is the majority polyglutamate and little longer-chain aminopterin is seen (compare Examples 52 and 53, and compare Examples 54 and 55).

In each lineage tested, the weighted average chain length of aminopterin is less than the weighted average chain length of methotrexate, reflecting the shift to shorter chain lengths of aminopterin compared to methotrexate. Previous studies showed that cell retention of an antifolate is proportional to the length of the polyglutamate chain [Kuehl, et al., *Cancer Res.* 48(6):1481, 1988]. Although aminopterin would be expected to be less efficacious than methotrexate based on these teachings, it has been found that the clinical use of aminopterin and its relative frequency pattern of polyglutamates to have a maximum level of efficacy equal to, and in some cases exceeding, the maximum level of efficacy of methotrexate and its relative frequency pattern of polyglutamates (see Examples 6-31 and 44-49). It has also been found that the clinical use of aminopterin and its relative frequency pattern of polyglutamates to have at least as large a therapeutic index, and in some cases a larger therapeutic index, than methotrexate and its relative frequency pattern of polyglutamates (see Examples 6-31).

Example 56

2,4-Diamino-6-pteridinemethanol (5) hydrobromide salt 2,4,5,6-Tetraminopyrimidine.H$_2$SO$_4$.H$_2$O (75.0 g, 0.293 mole) was added to a stirred solution of BaCl$_2$.2H$_2$O (71.5 g, 0.293 mole) in H$_2$O (1.45 l.) at 85-90° C. The mixture was stirred rapidly at about 90° C. for 15 min, cooled to 40° C., and filtered from BaSO$_4$, which was washed thoroughly on a funnel with H$_2$O. The clear, yellow filtrate was then diluted further with H$_2$O to give a volume of 4.35 l. This solution of the tetraminopyrimidine.2HCl was then added to a solution of NaOAc (4.35 l. of 4 N) in which dihydroxyacetone (79.3 g, 0.88 mole) and cysteine.HCl.H$_2$O (51.5 g, 0.293 mole) had just been dissolved. The resulting solution was stirred mechanically at room temperature while a slow stream of air was continuously passed through it for 26 hr. (Yellow-orange solid began separating after 2 hr.) The mixture was then kept in a refrigerator for 16 hr before the solid was collected, washed successively with cold H$_2$O, EtOH, and Et$_2$O before it was dried to constant weight in vacuo over P$_2$O$_5$ at 25° C. [The crude product mixture (47 g) was weighed in order to obtain an estimate of the volume of 48% HBr required to form hydrobromide salts.] A mechanically stirred mixture of the dried solid and EtOH (6.05 l.) was heated to 70° C., and a solution of 48% HBr (28 ml) in EtOH (490 ml) was added in a thin stream while the mixture was maintained at 70-75° C. The mixture was then refluxed for about 5 min with rapid stirring while nearly all of the solid dissolved. The hot solution was treated with Norit and filtered through a Celite mat. The clear yellow filtrate was kept in a refrigerator overnight while a first crop of orange-colored solid separated. The collected solid was washed with EtOH, then dried in vacuo (56° C. over P$_2$O$_5$) to give 17.2 g of product. The filtrate was concentrated by evaporation (rotary evaporator, H$_2$O aspirator, bath to 35° C.) to about 2 l. and then refrigerated to give a second crop, which was dried as before, of 10.2 g; total yield 27.4 g (34%). The $^1$H NMR spectrum of this material in CF$_3$CO$_2$D showed it to contain a barely detectable amount of methyl substituted 2,4-diaminopteridine.HBr as evidenced by very weak signals at δ2.83 (CH$_3$) and δ8.85 (pteridine ring H). Strong signals produced by the desired product occur at δ5.28 (6-CH$_2$O) and δ9.08 (C$_7$—H). The proportion of desired product to the methyl-substituted contaminant was estimated from the $^1$H NMR integrals to be 20:1. The $^1$H NMR spectrum also revealed retention of a small amount of EtOH in the product dried as described but not enough to interfere with the conversion of it to 2.

Example 57

2,4-Diamino-6-(bromomethyl)pteridine (2) hydrobromide salt from (5)

Bromine (59.6 g, 0.373 mole) was added drop wise over a 30-min period to a stirred solution of triphenylphosphine (97.7 g, 0.373 mole) in anhydrous 486 ml of dimethylacetamide (DMAC) kept at about 10° C. (ice bath) and protected from atmospheric moisture. (Bromine remaining in the funnel was rinsed with 10 ml of DMAC). A smooth suspension containing finely divided, crystalline triphenylphosphine dibromide resulted. The 2,4-diamino-6-pteridinemethanol.HBr (2) (25.4 g, 0.093 mole) described above was added in one portion through a powder funnel (with the aid of 10 ml DMAC). The ice bath was removed, and the stirred mixture was allowed to warm to 20-25° C. After about 1 hr, complete solution had occurred. The solution, which gradually developed a dark-red color, was kept at 20-25° C. for 1 hr longer and was then chilled (ice bath) before it was treated with EtOH (72 ml). After overnight refrigeration, the solvents were removed by evaporation in vacuo. The dark, semisolid residue was stirred with two 300-ml portions of benzene (to remove triphenylphosphine oxide), and each portion was removed from the benzene-insoluble product by decantation. The solid that remained was dissolved with stirring in glacial AcOH (660 ml) which had been preheated to 80° C. The mixture was kept in a bath at 80° C. until solution was complete. A tan crystalline solid separated as the dark solution was allowed to cool. Overnight refrigeration caused the AcOH to partially freeze. When it had thawed, the solid was collected, washed with chilled AcOH followed by Et$_2$O, and dried in vacuo (over P$_2$O$_5$ and NaOH pellets) at successive temperatures of 25° C., 56° C., and 110° C. (The higher temperature was necessary for complete removal of AcOH). The yield was 15.3 g (49%). (Some runs afforded 60% yield). This sample was further purified by reprecipitation from MeOH solution (Norit) by addition of Et$_2$O followed by drying in vacuo (25° C., P$_2$O$_5$), yield 13.0 g (42%) of pale-yellow solid. Spectral data: λmax, nm (ε×10$^{-3}$), 0.1 N HCl, 249 (17.3), 339 (10.5), 353 (sh); pH 7, 258 (21.2), 370 (6.87); 0.1 N NaOH, 258 (21.5), 370 (6.94); $^1$H NMR (CF$_3$CO$_2$D), δ 4.70 (s, 2, CH$_2$) and δ 9.08 (s, 1, C$_7$—H); estimated proportion relative to the methyl-substituted contaminant, 25:1. The preparation of 2 described above is typical of several runs that gave similar yields of material whose $^1$H NMR spectra differed only slightly in the estimated proportion of 2 with respect to the methyl-substituted contaminant. The proportions usually ranged from 16:1 to 25:1, which corresponds to a percentage of 2 of 94 to 96%.

Example 58

2,4-Diamino-6-(bromomethyl)pteridine (2) hydrobromide salt from (1)

A suspension of 5 mmol 2,4,5,6-tetraminopyrimidine dibromide in 50 ml methanol was treated with a solution of 7.5 mmol β-bromopyruvaldoxime in 10 ml of methanol at reflux temperature for 2 h. The 2,4-diamino-6-(bromomethyl)pteridine was collected after neutralization with concentrated $NH_3$ at room temperature, washed with methanol, ether and dried at 100° C. in an oven. $^1H$ NMR (250 MHz, ppm, DMSO-$d_6$), δ 8.84 (s, 1H, $C_7$—H). The yield was 88%.

Example 59

Active Pharmaceutical Ingredient Containing Aminopterin (4)

A mixture of 2 (168 mg, 0.500 mmole) and N-(4-aminobenzoyl)-L-glutamic acid, compound 3 (400 mg, 1.50 mmoles) in DMAC (2 ml) was stirred at 25° C. under $N_2$ in a stoppered flask protected from light. Solution occurred after 2 hrs. After 18 hrs, the orange solution was mixed with $H_2O$ (15 ml) with stirring to give a finely divided, yellow precipitate. The mixture was centrifuged, and the supernatant removed by decantation. The yellow solid was stirred with four 15-ml portions of $H_2O$, each of which was removed by decantation after centrifugation. The solid was then suspended in EtOH (15-20 ml), collected by filtration, washed with $Et_2O$, and dried in vacuo (25° C., $P_2O_5$) to give hydrated 4 in 68% yield (160 mg). Anal. Calc'd for $C_{19}H_{20}N_8O_5 \cdot 1.75H_2O$: C, 48.36; H, 5.02; N, 23.74. Found: C, 48.72; H, 4.91; N, 23.36. Spectral data: λmax, nm (ε×$10^{-3}$), 0.1 N HCl, 244 (18.2), 290 (20.5), 335 (11.0); pH 7, 260 (26.7), 283 (25.5), 370 (8.00); 0.1 N NaOH, 260 (26.9), 283 (25.3), 370 (8.00); $^1H$ NMR (DMSO-$d_6$), 62.02 (m, 2, CHCH$_2$CH$_2$), 2.32 (m, 2, CH$_2$CO$_2$H), 4.36 (m, 1, NHCHCO$_2$H), 4.52 (s, 2, CH$_2$N), 6.85 (m, 4, 2 phenylene protons plus NH$_2$), 7.72 (m, 2, phenylene), 7.86 (broad s, 2, NH$_2$), 8.13 (d, 1, NHCO), 8.72 (s, 1, $C_7$—H). Examination by tlc revealed one uv-absorbing spot and no fluorescence at any point. The product may be used directly as the active pharmaceutical ingredient, but is occasionally subjected to one or more re-crystallizations from water or formamide to improve the aminopterin purity slightly. The active pharmaceutical ingredient is stored in the presence of desiccant.

Examples 60-65

Analysis of Active Pharmaceutical Ingredient

Three different 1 mM solutions of a first batch of the active pharmaceutical ingredient prepared according to Example 59 were prepared by weighing out 2.3 mg, 4.5 mg and 1.8 mg of the active pharmaceutical ingredient as if it were 100% aminopterin (FW 440.42 g/mole), and dissolving it into 5.223 ml, 10.218 ml, and 4.087 ml of 0.001 N NaOH, respectively. Twenty μl of each 1 mM solution was subjected to HPLC analysis by injecting each onto a C18 column (Waters μBondapak 125 Å, 10 μm, 3.9×150 mm) using an isocratic mobile phase consisting of 5 mM PicA, 10 mM $NH_4H_2PO_4$ and 20% methanol at a pH of 6.8. The flow rate of the mobile phase was 1 ml/min, and the analysis was performed at room temperature. Using a Waters 996 PDA UV spectrophotometer, absorbance data from 210 nm to 400 nm was captured. The data was analyzed with the Waters Millennium software by extracting the chromatogram at 282 nm and calculating the peak area percentages. The data was also analyzed by extracting the spectra of individual peaks, allowing the identification of pABAGlu, folic acid, aminopterin and pterin species by their characteristic spectra.

The average of the HPLC analyses of the three separate 1 mM solutions revealed that the first batch of active pharmaceutical ingredient consisted of approximately 96.27 area % aminopterin and 3.73 area % impurities, wherein the impurities were made up of 0.23 area % folic acid, 2.18 area % N-(4-aminobenzoyl)-L-glutamic acid (i.e. pABAGlu), and 0.92 area % of a pterin, probably 2,4-Diamino-6-(bromomethyl)pteridine, and 0.4 area % of at least two other unidentified impurities (Example 60, Table XII). A similar HPLC analysis revealed that a second batch of active pharmaceutical ingredient consisted of 97.23 area % aminopterin and 2.775 area % impurities, wherein the impurities were made up of 1.82 area % folic acid, 0.556 area % N-(4-aminobenzoyl)-L-glutamic acid (i.e. pABAGlu), 0.343 area % pterin, probably 2,4-diamino-6-(bromomethyl)pteridine), and 0.056 area % of an unidentified impurity (Example 61, Table XII). By comparison, the prior art active pharmaceutical ingredients contained aminopterin and variable amounts of impurities ranging up to 41% (Examples 62-65, Table XII).

Example 66

Pharmaceutical Compositions

This example illustrates the preparation of pharmaceutical compositions substantially free of impurities. As used in this example, "API" means an active pharmaceutical ingredient substantially free of impurities, wherein the antifolate in the API is aminopterin, or a pharmaceutically acceptable salt thereof. The aminopterin purity of the API is used to established how much API is required in the pharmaceutical composition to obtained a desired final amount of aminopterin, or a pharmaceutically acceptable salt thereof, in the pharmaceutical composition.

Tablets: Surface deposit aminopterin by combining 16.8 grams API, 791.0 grams microcrystalline cellulose, 553.7 grams lactose monohydrate, 1.5 g NaOH and 632 grams of sterile water. Mix and dry overnight. Add 1311 grams of this surface deposited aminopterin to 171 grams of lactose, 3.9 grams colloidal silicon dioxide, 46.2 grams sodium croscarmellose, and 7.7 grams magnesium stearate to provide a total weight 1540 grams. Compress into approximately 15,000 tablets using a tableting machine, wherein each tablet weighs approximately 100 mg and contains about 1 mg aminopterin.

Gelatin capsules: Prepare by mixing 0.5 grams of API with 0.5 grams magnesium stearate, and 99 grams of lactose. Dispense 100 mg of this mixture into hard-shell gelatin capsules to provide each capsule with about 0.5 mg of aminopterin.

Suspension: An aqueous suspension is prepared for oral administration so that each 5 ml contains about 2 mg aminopterin by mixing 40 mg of API with 20 grams of sodium carboxymethyl cellulose, 0.5 grams of sodium benzoate, 100 grams of sorbitol solution U.S.P., and 2.5 ml of vanillin.

Liquid for injection or oral administration: Clean glassware to be used with 2 M NaOH for 3-5 minutes and the rinse thoroughly with deionized water. Prepare a first saline buffer by adding 2.7017 grams of dibasic sodium phosphate, USP to 5 liters of 0.9% sodium chloride for injection, USP. Prepare a second saline buffer by adding 1.39 grams of monobasic sodium phosphate, USP to 1 liter of 0.9% sodium chloride for injection, USP. While stirring the first saline buffer solution, slowly add the second saline buffer solution until the final pH is 7.9-8.1. Record the final volume. Add sufficient API to provide 0.4 mg/ml aminopterin (i.e. 2 mg aminopterin per 5 ml) and filter through a 0.2 micron membrane filter and package under sterile conditions in 10-ml vials each containing 5 ml. Use within 2 months.

Injectable: A parenteral formulation is prepared by mixing 0.200 grams of API with 20.0 grams of propylene glycol, 20.0 grams of polyethylene glycol 400, and 1.0 gram of polysorbate 80. A sufficient quantity of 0.9% saline solution is then added with stirring to provide 100 ml of solution which is filtered through a 0.2 micron membrane filter and packaged under sterile conditions in 2-ml vials each containing 1 ml, or a total of about 2 mg/vial aminopterin. The solution is diluted 10-fold with 0.9% saline solution prior to administration via an intravenous route.

Example 67

Mean and Standard Deviation of Dose in Pharmaceutical Compositions

The average dose and the dose uniformity (i.e. standard deviation) of aminopterin among 10 randomly selected tablets were determined for a batch of 15,000 1 mg aminopterin tablets prepared according to Example 66 (Table XIII). The mean dose and dose uniformity were obtained by scanning spectrophotometry and a radioligand binding assay using dihydrofolate reductase (DHFR) as binder and methotrexate as a standard.

For scanning spectrophotometry, each of ten tablets are dissolved in 11.35 ml of water by rotating in a 15 ml tube for 30 minutes at room temperature to make an approximately 200 µM solution (i.e. about 1 mg aminopterin with a FW of 440 g/mole in 11.35 ml). The tubes are spun, and a portion of the supernatant is diluted ten-fold with 0.1 N NaOH to a final concentration of 20 µM. The absorbance of the diluted supernatant is read at 282 nm and 260 nm on a Perkin-Elmer Lambda 4B scanning spectrophotometer (1 cm path length) and the concentration of the diluted sample calculated using the relationships, concentration (in µM) at 282 nm=10× $(OD_{282}/0.264)$ and concentration (in µM) at 260 nm=10× $(OD_{260}/0.285)$. The mg/ml at 282 nm and 260 nm is then calculated using the relationship, mg/ml=concentration (in µM)×0.00044. The total mg of aminopterin in each tablet is then determined by multiplying the mg/ml determined at 282 nm and 260 nm by 113.5. The mg of aminopterin per tablet is then reported as the average of the mg of aminopterin in each tablet determined at 282 nm and 260 nm. For example, using the above procedure, a 1 mg aminopterin tablet yields an $OD_{282}$ of 0.5227, and a calculated concentration (in EM), mg/ml, and total mg of aminopterin of 19.8 µM, 0.008712 mg/ml, and 0.9888 mg, respectively. Using the above procedure, the same 1 mg aminopterin tablet yields an $OD_{260}$ of 0.5641, and a calculated concentration (in EM), mg/ml, and total mg of aminopterin of 19.8 µM, 0.008712 mg/ml, and 0.9888 mg, respectively. The reported amount of aminopterin in the tablet is the mean of total aminopterin in the tablet calculated at 282 nm and 260 nm, or 0.9888 mg.

The radioligand binding assay was performed essentially as described previously for methotrexate [see Kamen et al., *Anal. Biochem.* 70:54, 1976 and Ratliff et al., *J. Clin. One.* 16:1458, 1998]. Briefly, a standard curve was developed for 0.2 to 1.0 pmol methotrexate binding to partially purified chicken liver DHFR, wherein binding of a known amount of non-radioactive methotrexate results in the displacement of an amount of tritiated methotrexate (i.e. radioactive $^3$H-methotrexate). Aminopterin and methotrexate are equivalent in the assay in terms of their displacement and binding, and the absolute detection limit of the assay is 0.05 to 0.10 pmol of antifolate. After the standard curve is established, a portion of the 200 µM supernatant prepared above for an aminopterin tablet is further diluted 10,000 using two serial 100-fold dilutions with water to provide an approximately 20 nM solution of aminopterin. The DHFR assay is performed with 100 µL of the 20 nM solution, as well as several 2-fold serial dilutions, and the result expressed as pmol/ml aminopterin. The total number of pmol of aminopterin is calculated using the relationship, pmol/ml×10,000×11.35. The total number of mg in the tablet is then calculated using the relationship, total pmol× $(10^{-6}$ µmole/pmol$)\times 0.44$ mg/µmole.

As determined by scanning spectrophotometry, the average dose and the dose uniformity (i.e. standard deviation) of aminopterin among 10 randomly selected tablets from a batch of 15,000 1 mg aminopterin tablets was 0.974 mg and 2.271%, respectively (Table XIII). As determined by radioligand binding assay, the average dose and the dose uniformity (i.e. standard deviation) of aminopterin among the same 10 tablets was 1.01 mg and 3.929%, respectively (Table XIII).

Example 68

The levels of aminopterin and methotrexate in the CSF were measured in subjects two to six hours after being dosed with aminopterin 2 mg/m$^2$ po or methotrexate 25 mg/m$^2$ po, respectively (i.e. the toxicity manifestation was the CSF antifolate level). The mean CSF methotrexate concentration (i.e. the toxicity component) of 18.63 nM (SD 9.87 nM), was significantly greater than the mean CSF aminopterin concentration of 3.000 nM (SD 1.054 nM), which was indistinguishable from control subjects (P<0.0001, two-tailed t-test). These differences likely represent steady-state antifolate levels, because over the course of the five lumbar punctures given during 12 weeks of consolidation, mean CSF methotrexate or aminopterin did not increase in these subjects. In other words, the toxicity component for the above toxicity manifestation (i.e. CSF antifolate) was lower for 4 mg/m$^2$/wk aminopterin than for 100 mg/m$^2$/wk methotrexate. These results demonstrate that aminopterin has a larger therapeutic index than methotrexate with respect to CNS toxicity. The implication is that patients administered a dose of aminopterin will experience less neurotoxicity than patients administered an equiefficacious dose of methotrexate (i.e. doses producing equivalent therapeutic manifestations).

Example 69

Antifolate uptake and excretion from major body organ systems including the brain was examined in an animal pharmacokinetic study after 4 weekly doses of aminopterin and methotrexate administered at their corresponding maximum anti-inflammatory dose, and at increasing times up to 22 days after the last dose given. Male mice (10-15 week-old) were given weekly intraperitoneal (ip) injections of vehicle (0.9% saline, control, n=60), aminopterin (0.03 mg/kg, n=60) or methotrexate (0.3 mg/kg, n=60) over the course of a month on days 1, 7, 14 and 21. On days 22 (+1), 24 (+3), 26 (+5), 29 (+8), 33 (+12), and 43 (+22), a group of n=5 animals was sacrificed from the vehicle, aminopterin and methotrexate arms of the study. Organs and fluids were removed from each animal, frozen, and the folate and antifolate content subsequently quantitated using a radioligand binding assay (i.e. the toxicity manifestation was antifolate content in the organ or fluid). Whereas the aminopterin and methotrexate content were no different in the livers of animals on days 1 and 22, the brain parenchyma of the animals contained significantly less antifolate on days 1, 12 and 22 in the aminopterin treated arm ($P<0.0001$; $P=0.0012$; $P<0.0001$, respectively). These results demonstrate that aminopterin has a larger therapeutic index than methotrexate with respect to CNS toxicity. The implication is that patients administered a dose of aminopterin will experience less neurotoxicity than patients administered an equiefficacious dose of methotrexate (i.e. doses producing equivalent therapeutic manifestations).

Example 70

Additional patients were accrued into the clinical trials of Examples 44-49 and a survival analysis was performed using a time-to-event curve using the Kaplan Meier method. The event-free survival (EFS) at 24-months of the 25 high risk patients receiving aminopterin was 93%, whereas the standard risk patients receiving methotrexate had an EFS of 86%. These clinical trial data support that aminopterin is more efficacious than methotrexate, and well tolerated over years.

The present invention is not to be limited in scope by the specific embodiments disclosed in the examples which are intended as illustrations of a number of aspects of the invention and any embodiments which are functionally equivalent are within the scope of this invention. Indeed, various modifications of the invention in addition to those shown and described herein will become apparent to those skilled in the art and are intended to fall within appended claims.

A number of references have been cited, the entire disclosures of which are incorporated herein by reference.

TABLE I

Interpatient oral bioavailability

|  | AMT = 2 mg/m$^2$ (pediatric patients) | AMT = 2 mg/m$^2$ (adult patients)* | MTX 15–25 mg/m$^2$ (pediatric patients)* |
|---|---|---|---|
| Number of patients | 15 | 13 | 22 |
| Minimum (%) | 45% | 32% | 6% |
| Maximum (%) | 165% | 163% | 95% |
| Interpatient oral bioavailability (%) | 94 | 85 | 44 |

*Prior art, not the subject invention [see Ratliff et al., J. Clin. Onc. 16: 1458, 1998; Balis, et al., Cancer Res. 43(5): 2342, 1983; Pinkerton, et al., Br. J. Cancer 45(2): 300, 1982; and Pinkerton, et al., Cancer Chemother. Pharmacol. 10(1): 36, 1982]. Abbreviations: AMT, aminopterin; and MTX, methotrexate.

TABLE II

| Example | Antifolate | Dose | Interpatient coefficient of variation of oral bioavailability |
|---|---|---|---|
| 2 | AMT | 2 mg/m$^2$ PO | 42% (n = 27) |
| 3* | MTX | 15–25 mg/m$^2$ PO | 59% (n = 22) |

*Not part of the subject invention. Abbreviations: PO, oral route of administration; 'n' is the number of patients; AMT, aminopterin; and MTX, methotrexate.

TABLE III

| Example | Antifolate | Dose | Mean intrapatient coefficient of variation of oral bioavailability |
|---|---|---|---|
| 4 | AMT | 2 mg/m$^2$ PO | 25% (n = 5) |
| 5* | MTX | 15–25 mg/m$^2$ PO | 34% (n = 38) |

*Not part of the subject invention. Abbreviations: PO, oral route of administration; 'n' is the number of patients; AMT, aminopterin; and MTX, methotrexate.

TABLE IV

| Example | Disease Manifestation | Antifolate | Therapeutic Component Antifolate dose: Percentage effective | Toxicity Manifestation | Toxicity Component Antifolate dose with same toxicity as MTX at 100 mg/m$^2$/wk | Therapeutic Index |
|---|---|---|---|---|---|---|
| 6 | Peripheral blasts and bone marrow infiltrates in T-lineage ALL (n = 7 patients) | AMT | 4 mg/m$^2$/wk: 43% complete remission or stable disease | Mucositis | 4 mg/m$^2$/wk | 1 |
| 7 | same | AMT | same | Neutropenia | 4 mg/m$^2$/wk | 1 |
| 8 | same | AMT | same | Thrombocytopenia | 4 mg/m$^2$/wk | 1 |
| 9 | same | AMT | same | Myelosuppression | 4 mg/m$^2$/wk | 1 |
| 10* | Peripheral blasts and bone marrow infiltrates in T-lineage ALL (n = 7 patients) | MTX | >5000 mg/m$^2$/wk: 0% effective in the same patients treated with AMT | Mucositis | 100 mg/m$^2$/wk | <0.02 |

TABLE IV-continued

| Example | Disease Manifestation | Antifolate | Therapeutic Component Antifolate dose: Percentage effective | Toxicity Manifestation | Toxicity Component Antifolate dose with same toxicity as MTX at 100 mg/m²/wk | Therapeutic Index |
|---|---|---|---|---|---|---|
| 11* | same | MTX | same | Neutropenia | 100 mg/m²/wk | <0.02 |
| 12* | same | MTX | same | Thrombo-cytopenia | 100 mg/m²/wk | <0.02 |
| 13* | same | MTX | same | Myelo-suppression | 100 mg/m²/wk | <0.02 |

*Not part of the subject invention. Abbreviations: ALL, acute lymphoblastic leukemia; AMT, aminopterin; and MTX, methotrexate.

TABLE V

| Example | Disease Manifestation | Antifolate | Therapeutic Component Antifolate dose: Percentage effective | Toxicity Manifestation | Toxicity Component Antifolate dose with same toxicity as MTX at 100 mg/m²/wk | Therapeutic Index |
|---|---|---|---|---|---|---|
| 14 | Peripheral blasts and bone marrow infiltrates in high risk ALL (n = 20) | AMT | 4 mg/m²/wk: 100% effective at greater than 12 months treatment | Mucositis | 4 mg/m²/wk | 1 |
| 15 | same | AMT | same | Neutropenia | 4 mg/m²/wk | 1 |
| 16 | same | AMT | same | Thrombo-cytopenia | 4 mg/m²/wk | 1 |
| 17 | same | AMT | same | Myelosuppression | 4 mg/m²/wk | 1 |
| 18 | same | AMT | same | Hospital admissions | 4 mg/m²/wk | 1 |
| 19 | same | AMT | same | Treatment interruptions | 4 mg/m²/wk | 1 |
| 20 | same | AMT | same | eAMT and eMTX (marrow exposure) | 4 mg/m²/wk | 1 |
| 21 | same | AMT | same | Any elevation of liver enzymes | 4 mg/m²/wk | 1 |
| 22* | Peripheral blasts and bone marrow infiltrates in standard risk ALL (n = 20) | MTX | 100 mg/m²/wk: 100% effective at greater than 12 months treatment | Mucositis | 100 mg/m²/wk | 1 |
| 23* | same | MTX | same | Neutropenia | 100 mg/m²/wk | 1 |
| 24* | same | MTX | same | Thrombo-cytopenia | 100 mg/m²/wk | 1 |
| 25* | same | MTX | same | Myelosuppression | 100 mg/m²/wk | 1 |
| 26* | same | MTX | same | Hospital admissions | 100 mg/m²/wk | 1 |
| 27* | same | MTX | same | Treatment interruptions | 100 mg/m²/wk | 1 |
| 28* | same | MTX | same | eAMT and eMTX (marrow exposure) | 100 mg/m²/wk | 1 |
| 29* | same | MTX | same | Any elevation of liver enzymes | 100 mg/m²/wk | 1 |

*Not part of the subject invention. Abbreviations: ALL, acute lymphoblastic leukemia; AMT, aminopterin; MTX, methotrexate; eAMT, erythrocyte aminopterin; and eMTX, erythrocyte methotrexate.

TABLE VI

| Example | Disease Manifestation | Antifolate | Therapeutic Component Antifolate dose with same efficacy as MTX at 100 mg/m²/wk | Toxicity Manifestation | Toxicity Component Antifolate dose causing 5.8% of the population to have the toxicity | Therapeutic Index |
|---|---|---|---|---|---|---|
| 30 | Peripheral blasts and bone marrow infiltrates in high risk ALL; (n = 20) | AMT | 4 mg/m²/wk | Elevations in liver enzymes >5 times normal | 4 mg/m²/wk (n = 104) | 1 |

TABLE VI-continued

| Example | Disease Manifestation | Antifolate | Therapeutic Component Antifolate dose with same efficacy as MTX at 100 mg/m²/wk | Toxicity Manifestation | Toxicity Component Antifolate dose causing 5.8% of the population to have the toxicity | Therapeutic Index |
|---|---|---|---|---|---|---|
| 31* | Peripheral blasts and bone marrow infiltrates in standard risk ALL; (n = 20) | MTX | 100 mg/m²/wk | Elevations in liver enzymes >5 times normal | <100 mg/m²/wk (i.e. 100 mg/m²/wk causes 11.1% of the population to have the toxicity, n = 63) | <1 |

*Not part of the subject invention. Abbreviations: 'n' is the number of determinations; ALL, acute lymphoblastic leukemia; AMT, aminopterin; and MTX, methotrexate.

TABLE VII

| Example | Toxicity Manifestation | Antifolate | Dose | Mean§ | Standard Deviation | Coefficient of variation of toxicity | Relative To The Invention |
|---|---|---|---|---|---|---|---|
| 32 | Level of liver enzymes above normal | AMT | 2 mg/m² PO × 2 (n = 104) | 188 | 47 | 25% | 1.0 |
| 33* | Level of liver enzymes above normal | MTX | 25 mg/m² PO × 4 (n = 63) | 177 | 63 | 36% | 1.4 |
| 34 | Level of erythrocyte antifolate | AMT | 2 mg/m² PO × 2 (n = 43) | 203 | 136 | 67% | 1.0 |
| 35* | Level of erythrocyte antifolate | MTX | 25 mg/m² PO × 4 (n = 22) | 225 | 272 | 121% | 1.8 |
| 36* | Level of erythrocyte antifolate | MTX | 25 mg/m² PO × 4 (n = 57) | 287 | 301 | 105% | 1.6 |
| 37* | Level of erythrocyte antifolate | MTX | 1000 mg/m² IV (n = 23) | 270 | 384 | 142% | 2.1 |
| 38* | Level of erythrocyte antifolate | MTX | 20 mg/m² IM (n = 32) | 180 | 622 | 346% | 5.2 |
| 39* | Level of erythrocyte antifolate | MTX | 20 mg/m² PO (n = 48) | 90 | 484 | 538% | 8.0 |
| 40 | Absolute neutrophil count in consolidation | AMT | 2 mg/m² PO × 2 (n = 75) | 1667 | 1332 | 80% | 1.0 |
| 41* | Absolute neutrophil count in consolidation | MTX | 25 mg/m² PO × 4 (n = 41) | 1919 | 1630 | 85% | 1.1 |
| 42 | Platelet counts in consolidation | AMT | 2 mg/m² PO × 2 (n = 81) | 316 | 184 | 58% | 1.0 |
| 43* | Platelet counts in consolidation | MTX | 25 mg/m² PO × 4 (n = 42) | 312 | 145 | 47% | 0.81 |

*Not part of the subject invention. Abbreviations: PO, oral route of administration; IV, intravenous route of administration; IM, intramuscular route of administration; 'n' is the number of determinations; AMT, aminopterin; and MTX, methotrexate.
§Units for each toxicity manifestation are: IU/L ALT, level of liver enzymes above normal; pmol/ml RBC, level of erythrocyte antifolate; cells/μL, absolute neutrophil count in consolidation; and cells × 10³/μL, platlet counts in consolidation.

TABLE VIII

| Example 44* | Example 45 |
|---|---|
| CONSOLIDATION (weeks 5–15) Standard Risk ALL MTX: Divided dose oral MTX (dMTX); 25 mg/m²/dose, given every six hours for four doses on weeks 5, 6, 7, 8, 9, 10, 11, 12, 13, 14, and 15. Note: during weeks when ITT given, use the ITT as the fourth dose of oral MTX, e.g., MTX po at 6 pm on Monday; MTX po at midnight; MTX po Tuesday at 6 am; ITT at noon Tuesday. No leucovorin given during the weeks that patients receive ITT therapy. Each week of MTX therapy requires ANC >500/μl and platelets >75,000/μl; | CONSOLIDATION (weeks 5–15) High Risk ALL AMT: Divided dose oral AMT (dAMT); 2 mg/m²/dose, given every twelve hours for two doses weeks 5, 6, 7, 8, 9, 10, 11, 12, 13, 14, and 15 . . . Note: on weeks that ITT is given (weeks 6, 8, 10, 12, and 14), ITT should follow the second dose of dAMT by 4 to 12 hours. Each week of AMT therapy requires ANC >500/μl and platelets >75,000/μl; bilirubin <1.7 mg/dl; ALT <20 × upper limit of normal and creatinine normal for age. Leucovorin: Single oral dose (5 mg/m²/dose) taken 48 hours |

TABLE VIII-continued

| Example 44* | Example 45 |
|---|---|
| bilirubin <1.7 mg/dl; ALT <20 × upper limit of normal and creatinine normal for age. Leucovorin: Two oral doses (5 mg/m²/dose) is given q 12 h beginning 48 hours after the start of the dMTX every other week (no leucovorin given following dMTX on the weeks that ITT therapy is given). 6-mercaptopurine: Twice daily oral doses of 6-MP (37.5 mg/m²/dose) given q am and qhs each day during consolidation. ITT: Dose by age on weeks 6, 8, 10, 12, and 14. | after the first oral AMT dose. (No leucovorin given following dAMT on the weeks that ITT therapy is given, i.e. weeks 6, 8, 10, 12, and 14.) 6-mercaptopurine: Twice daily oral doses of 6-MP (37.5 mg/m²/dose) given q am and qhs each day during consolidation. ITT: Dose by age on weeks 6, 8, 10, 12, and 14. ITT should be given between 4 and 12 hours after second dose of divided dose AMT. |

*Not part of the subject invention. Abbreviations: po, oral route of administration; q, every; h, hours; am, morning; hs, evening; ANC, absolute neutrophil count; ALT, alanine aminotransferase; μl, microliter; dl, deciliter; d, divided; ITT, triple intrathecal therapy; AMT, aminopterin; and MTX, methotrexate.

TABLE IX

| Example 46* | Example 47 |
|---|---|
| INTENSIVE CONTINUATION (weeks 16–79) Standard Risk ALL Repeat the 8 week cycle 8 times (about 64 weeks). MTX: MTX at 25 mg/m²/dose is given every 6 hours × 4 doses on weeks 1, 3, and 7 of each 8 week intensive continuation therapy cycle. Leucovorin: 5 mg/m² po q 12 h × 2 beginning 48 hours after the start of the dMTX. 6-mercaptopurine (6-MP): BID 6-MP at 37.5 mg/m²/dose given twice daily throughout intensive continuation therapy. L-asparaginase: 10,000 IU/m² given IM 24 hours after the first dose of dMTX (six hours after the fourth dose), on weeks 1, 3, 5, and 7 of the first four 8-week cycles only. Vincristine: Vincristine 1.5 mg/m²IV push × 1 dose; day 1 week 8. Dexamethasone: 6 mg/m²/day po divided BID × 7 days, beginning day 1, week 8. ITT: week 8 of each intensive continuation cycle. | INTENSIVE CONTINUATION (weeks 24–87) High Risk ALL Repeat the 8 week cycle 8 times (about 64 weeks). AMT: AMT 2 mg/m²/dose is given every 12 hours × 2 doses on weeks 1, 3, 5, and 7 of each 8 week intensive continuation therapy cycle. Note: on weeks that ITT is given (week 3 of cycles 1 through 4), ITT follows the second dose of dAMT by 4 to 12 hours. Leucovorin: Single oral dose (5 mg/m²/dose) taken 48 hours after the first oral AMT dose. (No leucovorin given following dAMT on weeks ITT therapy is given.) 6-mercaptopurine (6-MP): BID 6-MP at 37.5 mg/m²/dose given twice daily throughout intensive continuation. L-asparaginase: 10,000 IU/m² given IM 24 hours after the first dose of dAMT, on weeks 1, 3, 5 and 7 of the first four cycles only. Vincristine: 1.5 mg/m² IV push × 1 dose; day 1 week 8. (maximum dose 2.0 mg IV Push) Dexamethasone: 6 mg/m²/day po divided BID × 7 days, starting day 1, week 8. ITT Dose by age weeks 3 and 8 of the first four cycles of intensive continuation cycles and then on week 8 only of cycles 5–8 of intensive continuation. ITT should be given between 4 and 12 hours after second dose of divided dose AMT. Note: no intrathecal chemotherapy given after craniospinal irradiation. Only those high-risk patients who did not receive craniospinal radiation continue ITT. |

*Not part of the subject invention. Abbreviations: po, oral route of administration; q, every; h, hours; IM, intramuscular; IV, intravenous; IU, international units; BID, twice daily; d, divided; ITT, triple intrathecal therapy; AMT, aminopterin; and MTX, methotrexate.

TABLE X

| Example 48* | Example 49 |
|---|---|
| CONTINUATION (weeks 80–135) Standard Risk ALL MTX: A single dose of oral MTX at 40 mg/m² given weekly qhs. MTX will not be given during week that ITT is given. 6-Mercaptopurine: 37.5 mg/m²/dose po BID (am and hs; total dose = 75 mg/m²/day). ITT: During week 8 of every 8 week continuation cycle. Final ITT (week 135 may be omitted and surveillance lumbar puncture only done at 3–4 weeks after cessation of therapy). | CONTINUATION (weeks 88–135) High Risk ALL AMT: A single dose of oral AMT at 2 mg/m² will be given weekly qhs. AMT will not be given during week of triple intrathecal therapy. 6-Mercaptopurine: 37.5 mg/m²/dose po BID (am and hs; total dose = 75 mg/m²/day). ITT: Week 8 of every 8 week continuation cycle, except the last cycle. The final ITT is omitted, and a surveillance LP will be performed 3–4 weeks after cessation of therapy. Note: no intrathecal chemotherapy will be given after craniospinal irradiation. Only high-risk patients who did not receive craniospinal radiation continue to receive ITT. |

*Not part of the subject invention. Abbreviations: po, oral route of administration; q, every; am, morning; h, hours; hs, evening; IM, intramuscular; IV, intravenous; IU, international units; BID, twice daily; LP, lumbar puncture; ITT, triple intrathecal therapy; AMT, aminopterin; and MTX, methotrexate.

TABLE XI

| Example | Antifolate | Number of Patients | Lineage | $(glu)_1$ | $(glu)_2$ | $(glu)_3$ | $(glu)_4$ | $(glu)_5$ | weighted average chain length |
|---|---|---|---|---|---|---|---|---|---|
| 50 | AMT | 24 | Pre-B ALL | 2 | 32 | 29 | 20 | 16 | 3.13 |
| 51* | MTX | 23 | Pre-B ALL | 11 | 7 | 16 | 21 | 47 | 3.92 |

TABLE XI-continued

| Example | Antifolate | Number of Patients | Lineage | (glu)$_1$ | (glu)$_2$ | (glu)$_3$ | (glu)$_4$ | (glu)$_5$ | weighted average chain length |
|---|---|---|---|---|---|---|---|---|---|
| 52 | AMT | 13 | T-ALL | 6 | 62 | 22 | 7 | 2 | 2.34 |
| 53* | MTX | 11 | T-ALL | 30 | 16 | 30 | 24 | 17 | 3.33 |
| 54 | AMT | 12 | AML | 10 | 75 | 15 | 1 | 1 | 2.14 |
| 55* | MTX | 6 | AML | 31 | 25 | 34 | 12 | 6 | 2.61 |

*Not part of the subject invention. Abbreviations: AMT, aminopterin; MTX, methotrexate; (glu)$_1$, free drug (either AMT or MTX); (glu)$_2$, one glutamate added to free drug; (glu)$_3$, two glutamates added to free drug; (glu)$_4$, three glutamates added to free drug; and (glu)$_5$, four glutamates added to free drug. For each free drug and polyglutamate species (i.e. (glu)$_1$ through (glu)$_5$), the values in the table given for each example indicate the average molar fraction of the total intracellular antifolate that is the drug or polyglutamate species in the patient population.

TABLE XII

| Example | AMT purity | AMT total impurities | Composition of total impurities |
|---|---|---|---|
| 60 | 96.27% | 3.730% | FA (0.23%); pABAGlu (2.18%); pterins (0.92%); other (0.4%) |
| 61 | 97.23% | 2.775% | FA (1.82%); pABAGlu (0.556%); pterins (0.343%); other (0.056%) |
| 62*,$^a$ | 70–80% | 20–30% | not specified |
| 63*,$^b$ | <80% | >20% | FA (20%); others unspecified |
| 64*,$^c$ | 80% | 20% | FA (15%); pterins (5%) |
| 65*,$^d$ | 59% | 41% | not specified |

Percentages are HPLC peak areas.
Abbreviations: FA, folic acid; AMT, aminopterin; and pABAGlu, N-(4-aminobenzoyl)-L-glutamic acid.
*Not part of the subject invention.
$^a$Seeger, et al., J. Am. Chem. Soc. 71: 1753, 1949.
$^b$Heinrich et al., J. Am. Chem. Soc. 75: 5425.
$^c$Loo, J. Med. Chem. 8: 139, 1965.
$^d$Sirotnak and Donsbach, Biochem. Pharmacol. 24: 156, 1975.

TABLE XIII

| Random Tablet | AMT dose by spectro-photometry (mg) | AMT dose by radioligand binding assay (mg) |
|---|---|---|
| 1 | 0.99 | 1.03 |
| 2 | 0.98 | 0.93 |
| 3 | 0.99 | 1.04 |
| 4 | 0.97 | 1.04 |
| 5 | 0.94 | 0.96 |
| 6 | 0.96 | 1.05 |
| 7 | 0.99 | 0.99 |
| 8 | 0.94 | 1.03 |
| 9 | 0.97 | 1.01 |
| 10 | 1.01 | 1.03 |
| mean | 0.974 | 1.01 |
| standard deviation | 2.271% | 3.929% |

Abbreviations: AMT, aminopterin.

What is claimed is:

1. A method for treating a disorder in a patient, comprising administering to said patient a pharmaceutical composition comprising a therapeutically effective amount of aminopterin, or a pharmaceutically acceptable salt thereof, wherein the disorder is refractory acute lymphoblastic leukemia.

2. The method of claim 1, wherein a second drug is used in combination therapy and a second drug is an anti-neoplastic or anti-inflammatory drug.

3. The method of claim 1, wherein the patient is a pediatric patient.

* * * * *